US008394337B2

(12) United States Patent
Neel et al.

(10) Patent No.: US 8,394,337 B2
(45) Date of Patent: Mar. 12, 2013

(54) TEST STRIP CONTAINER WITH INTEGRATED METER

(75) Inventors: Gary T. Neel, Weston, FL (US); Brent E. Modzelewski, Boca Raton, FL (US); Cameron Scott Casterline, Pembroke Pines, FL (US); George R. Rounds, Coconut Creek, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 916 days.

(21) Appl. No.: 11/254,881

(22) Filed: Oct. 21, 2005

(65) Prior Publication Data
US 2006/0094986 A1 May 4, 2006

Related U.S. Application Data

(63) Continuation-in-part of application No. 10/857,917, filed on Jun. 2, 2004, now Pat. No. 8,147,426.

(60) Provisional application No. 60/533,557, filed on Dec. 31, 2003.

(51) Int. Cl.
| | |
|---|---|
| *B01L 3/00* | (2006.01) |
| *G01N 31/22* | (2006.01) |
| *G01N 33/52* | (2006.01) |
| *G01N 21/75* | (2006.01) |
| *G01N 35/00* | (2006.01) |
| *G01N 15/06* | (2006.01) |
| *G01N 33/00* | (2006.01) |
| *G01N 33/48* | (2006.01) |
| *G01N 21/00* | (2006.01) |
| *G01N 25/08* | (2006.01) |

(52) U.S. Cl. ....... 422/430; 422/401; 422/404; 422/68.1; 422/82.05; 436/150

(58) Field of Classification Search .................. None
See application file for complete search history.

(56) References Cited

U.S. PATENT DOCUMENTS
2,072,796 A    3/1937   Christopher
(Continued)

FOREIGN PATENT DOCUMENTS
| | | |
|---|---|---|
| EP | 1 288 653 A1 | 3/2003 |
| EP | 1 352 611 A1 | 10/2003 |

(Continued)

OTHER PUBLICATIONS

International Search Report from PCT/US2006/040706 dated Mar. 8, 2007 (4 pages).

(Continued)

Primary Examiner — Jill Warden
Assistant Examiner — Charles D Hammond
(74) Attorney, Agent, or Firm — Finnegan, Henderson, Farabow, Garrett & Dunner LLP

(57) ABSTRACT

A system for diagnostic testing may include a meter for performing a diagnostic test on a sample applied to a test media and a container configured to contain test media compatible with the meter. The meter may include a closure portion for selectively closing the opening of the container. The system may further provide a sampling device, such as a lancet, operable connected to the container such that that a user may use the sampling device to obtain a sample without disconnecting the sampling device from the container. The system may also provide mechanisms for removing a meter from a test container and reattaching it to a new one using one of several coding methods that recalibrate the meter for the new container of test strips. In addition, the system may further provide mechanisms to reconfigure the meter to perform a new function when it has been determined that the triggering event has occurred.

12 Claims, 18 Drawing Sheets

U.S. PATENT DOCUMENTS

| | | |
|---|---|---|
| 3,964,871 A | 6/1976 | Hochstrasser |
| 4,059,407 A | 11/1977 | Hochstrasser |
| 4,218,421 A | 8/1980 | Mack et al. |
| 4,615,462 A | 10/1986 | Sacherer et al. |
| 4,627,445 A | 12/1986 | Garcia et al. |
| 4,637,403 A | 1/1987 | Garcia et al. |
| 4,690,801 A | 9/1987 | Anderson |
| 4,717,018 A | 1/1988 | Sacherer et al. |
| 4,757,022 A | 7/1988 | Shults et al. |
| 4,787,398 A | 11/1988 | Garcia et al. |
| 4,797,256 A | 1/1989 | Watlington, IV |
| 4,834,234 A | 5/1989 | Sacherer et al. |
| 4,871,258 A | 10/1989 | Herpichboehm et al. |
| 4,876,068 A | 10/1989 | Castaneda |
| 4,877,580 A | 10/1989 | Aronowitz et al. |
| 4,905,866 A | 3/1990 | Bartell et al. |
| 4,934,556 A | 6/1990 | Kleissendorf |
| 4,995,402 A | 2/1991 | Smith et al. |
| 5,087,556 A | 2/1992 | Ertinghausen |
| 5,096,669 A | 3/1992 | Lauks et al. |
| 5,104,619 A | 4/1992 | de Castro |
| 5,108,889 A | 4/1992 | Smith et al. |
| 5,149,505 A | 9/1992 | English et al. |
| 5,279,294 A | 1/1994 | Anderson et al. |
| 5,413,764 A | 5/1995 | Haar |
| 5,429,804 A | 7/1995 | Sayles |
| 5,464,118 A | 11/1995 | Grau et al. |
| D367,109 S | 2/1996 | Ryner et al. |
| 5,489,414 A | 2/1996 | Schreiber et al. |
| 5,510,266 A | 4/1996 | Bonner et al. |
| 5,575,403 A | 11/1996 | Charlton et al. |
| 5,589,045 A | 12/1996 | Hyodo |
| 5,628,890 A | 5/1997 | Carter et al. |
| 5,630,986 A | 5/1997 | Charlton et al. |
| 5,639,424 A | 6/1997 | Rausnitz |
| 5,645,798 A | 7/1997 | Schreiber et al. |
| 5,649,642 A | 7/1997 | Mabry et al. |
| 5,695,623 A | 12/1997 | Michel et al. |
| 5,709,838 A | 1/1998 | Porter et al. |
| 5,728,352 A | 3/1998 | Poto et al. |
| 5,736,103 A | 4/1998 | Pugh |
| 5,738,244 A | 4/1998 | Charlton et al. |
| 5,791,514 A | 8/1998 | Kirk, III et al. |
| 5,795,543 A | 8/1998 | Poto et al. |
| 5,810,199 A | 9/1998 | Charlton et al. |
| 5,821,399 A | 10/1998 | Zelin |
| 5,854,074 A | 12/1998 | Charlton et al. |
| 5,856,195 A | 1/1999 | Charlton et al. |
| 5,872,713 A | 2/1999 | Douglas et al. |
| 5,904,898 A | 5/1999 | Markart |
| 5,950,865 A | 9/1999 | Menes |
| 5,951,492 A | 9/1999 | Douglas et al. |
| 5,989,917 A | 11/1999 | McAleer et al. |
| 6,036,924 A | 3/2000 | Simons et al. |
| 6,099,484 A | 8/2000 | Douglas et al. |
| 6,106,780 A | 8/2000 | Douglas et al. |
| 6,135,314 A | 10/2000 | Menes |
| 6,159,424 A | 12/2000 | Kauhaniemi et al. |
| 6,176,119 B1 | 1/2001 | Kintzig |
| 6,180,063 B1 | 1/2001 | Markart |
| 6,192,891 B1 | 2/2001 | Gravel et al. |
| 6,283,982 B1* | 9/2001 | Levaughn et al. ............ 606/172 |
| 6,300,142 B1 | 10/2001 | Andrewes et al. |
| 6,315,738 B1 | 11/2001 | Nishikawa et al. |
| 6,319,209 B1 | 11/2001 | Kriz |
| 6,352,514 B1 | 3/2002 | Douglas |
| 6,379,317 B1 | 4/2002 | Kintzig et al. |
| 6,540,675 B2 | 4/2003 | Aceti et al. |
| 6,544,475 B1 | 4/2003 | Douglas et al. |
| 6,558,897 B2 | 5/2003 | Scheuringer |
| 6,581,799 B1 | 6/2003 | Garrant et al. |
| 6,612,461 B2 | 9/2003 | Layer et al. |
| 6,623,698 B2 | 9/2003 | Kuo |
| 6,669,908 B2 | 12/2003 | Weyker et al. |
| 6,682,704 B2 | 1/2004 | Bottwein et al. |
| D487,594 S | 3/2004 | Alscher et al. |
| 6,743,635 B2 | 6/2004 | Neel et al. |
| 6,814,844 B2 | 11/2004 | Bhullar et al. |
| 6,997,343 B2* | 2/2006 | May et al. ..................... 221/232 |
| 6,997,344 B2* | 2/2006 | Brown et al. .................. 221/258 |
| 7,092,891 B2 | 8/2006 | Maus et al. |
| 7,998,407 B2* | 8/2011 | Wohland ....................... 422/404 |
| 2002/0057993 A1 | 5/2002 | Maisey et al. |
| 2002/0060247 A1 | 5/2002 | Krishnaswamy et al. |
| 2002/0150501 A1 | 10/2002 | Robertson et al. |
| 2002/0188224 A1 | 12/2002 | Roe et al. |
| 2003/0031591 A1 | 2/2003 | Whitson et al. |
| 2003/0031595 A1 | 2/2003 | Kirchhevel et al. |
| 2003/0032190 A1 | 2/2003 | Brown et al. |
| 2003/0036200 A1 | 2/2003 | Charlton |
| 2003/0059350 A1 | 3/2003 | Sacherer |
| 2003/0109777 A1 | 6/2003 | Kloepfer et al. |
| 2003/0129088 A1 | 7/2003 | Lee et al. |
| 2003/0133847 A1* | 7/2003 | Hagen et al. .................. 422/104 |
| 2003/0161762 A1 | 8/2003 | Caron et al. |
| 2003/0175155 A1 | 9/2003 | Charlton |
| 2003/0185705 A1 | 10/2003 | Otake |
| 2003/0185708 A1 | 10/2003 | Otake |
| 2003/0186446 A1 | 10/2003 | Pugh |
| 2003/0191415 A1 | 10/2003 | Moerman et al. |
| 2003/0207454 A1 | 11/2003 | Eyster et al. |
| 2003/0208140 A1 | 11/2003 | Pugh |
| 2003/0211625 A1 | 11/2003 | Cohen et al. |
| 2003/0212345 A1 | 11/2003 | McAllister et al. |
| 2003/0219357 A1 | 11/2003 | Douglas et al. |
| 2003/0223906 A1 | 12/2003 | McAllister et al. |
| 2004/0007585 A1 | 1/2004 | Griffith et al. |
| 2004/0047764 A1 | 3/2004 | Purcell |
| 2004/0048394 A1 | 3/2004 | Kirchhevel |
| 2004/0244151 A1 | 12/2004 | Sakata et al. |
| 2005/0009126 A1 | 1/2005 | Andrews et al. |
| 2005/0019953 A1 | 1/2005 | Groll |
| 2005/0143675 A1 | 6/2005 | Neel et al. |
| 2010/0004522 A1* | 1/2010 | Varela ........................... 600/347 |

FOREIGN PATENT DOCUMENTS

| | | |
|---|---|---|
| JP | 2000/019147 | 1/2000 |
| WO | WO 94/10558 | 5/1994 |
| WO | WO 96/13707 | 5/1996 |
| WO | WO 97/29847 | 8/1997 |
| WO | WO 99/59657 | 11/1999 |
| WO | WO 01/23885 | 4/2001 |
| WO | WO 02/078533 A2 | 10/2002 |
| WO | WO 02/088739 A1 | 11/2002 |
| WO | WO 03/042691 A1 | 5/2003 |
| WO | WO 03/082091 | 10/2003 |
| WO | WO 2005/102154 | 11/2005 |

OTHER PUBLICATIONS

International Search Report in PCT/US2004/042724, Home Diagnostics, Inc., dated Dec. 21, 2004.

Office Action dated Aug. 24, 2009, in co-pending U.S. Appl. No. 11/352,209, filed Feb. 13, 2006.

* cited by examiner

TEST STRIP CONTAINER WITH INTEGRATED METER

The present application is a continuation in part of U.S. application Ser. No. 10/857,917, filed Jun. 2, 2004 now U.S. Pat. No. 8,147,426, and claims the benefit of copending Provisional U.S. Patent Application 60/533,557, entitled "TEST STRIP CONTAINER WITH INTEGRATED METER," filed Dec. 31, 2003, both of which are incorporated herein by reference in their entirety.

The present invention is also related to U.S. Design Pat. Nos. D506,832, issued Jun. 28, 2005, and D507,657, issued Jul. 19, 2005, both entitled "METER FOR AN INTEGRATED DIAGNOSTIC TEST SYSTEM," which are incorporated herein by reference in their entirety.

TECHNICAL FIELD

The present invention relates to the field of diagnostic testing and, more particularly, to diagnostic testing systems using electronic meters.

BACKGROUND

Diagnostic testing systems are commonly used to perform various types of diagnostic tests on various types of samples. The diagnostic test may be a qualitative or quantitative test to determine the presence, concentration or amount of one or more analytes in a sample. The analyte may be a medically significant analyte—e.g., glucose, ketones, cholesterol, triglycerides, human choriogonadotropin (HCG), hemoglobin A1C, fructosamine, carbohydrates, tumor markers, lead, anti-epilepsy drugs, bilirubin, liver function markers, toxins or their metabolites, controlled substances, blood coagulation factors (PT, ATPP), etc.—contained in a biological sample—e.g., blood, urine, tissue, saliva, etc. However the diagnostic test is not limited to the medical field. For instance, the diagnostic test may determine the presence or quantity of an analyte in a water, soil or chemical sample.

Such diagnostic testing systems may include a test media (e.g., a test strip, tab, disc, etc.) configured to react to the presence of the analyte in a sample, and a separate electronic meter configured to interface with the test media in order to conduct the diagnostic test and indicate the results of the diagnostic test to the user.

In order to conduct the diagnostic test, a user must first obtain a sample test media, e.g., a test strip, from a container, then obtain a sample using a sampling device (e.g., by drawing blood using a lancet), and then apply the sample to the test media (either before or after inserting the test media into the meter interface). The meter then performs the diagnostic test on the sample and indicates the result to the user, e.g., using a numerical display.

However, the diagnostic meter is often bulky. Further, because the user must pick up and put down the test media container, sampling device and meter in succession, the test media container, sampling device and meter are easily separated from each other, so that users may find themselves without one or more of the components necessary to conduct the diagnostic test. Further, it is inconvenient for the user to carry a separate test media container, electronic meter and sampling device.

Further, test media from different brands or manufacturing lots may respond differently to the presence or concentration of analyte in the sample. In order to obtain more accurate results, the electronic meter may be calibrated with respect to a given brand or lot of test strips by providing it with one or more brand- or lot-specific calibration parameters that correlate the response from particular a particular brand or lot of test media to a standardized reference.

The user may be required to provide the meter with the appropriate calibration parameters in a separate "coding" step. For example, the test media container may display a code number from which the meter can determine the appropriate calibration information. The user may then manually enter the code number (e.g., using buttons or other user input devices on the meter) so as to provide the calibration data to the meter. Alternatively, the calibration data may be downloaded, e.g., from a manufacturer's website. In another approach, the test media container may be provided with an associated code chip in which the calibration data is stored electronically. The user may provide the calibration data to the meter by inserting the code chip into a corresponding port on the meter.

This coding step can be inconvenient or difficult for the user. For example, elderly or infirm users may have difficulty downloading calibration data or inserting code chips. Further, users may forget to calibrate the meter for use with a new brand or lot of test media. Consequently, the user may enter incorrect calibration parameters or codes, or the user may use test media from one brand or lot with a meter calibrated for use with test media from a different brand or lot. In addition, once a meter is calibrated for a given lot of test media, the use of that meter with test media from another lot may lead to erroneous results that could have serious consequences for the user. For example, where the test is a self-test of blood glucose level, an erroneous result can misinform the user as to their blood glucose level, which may lead to the user having a diabetic seizure.

A possible solution to the above-mentioned coding problems is utilizing the method of universal coding. This method uses strip lots that are controlled and sorted to a narrow acceptance criteria, i.e. all strips are conformed to a single set of calibration parameters, thus not requiring strip coding or more than one fixed set of strip lot parameters to be stored in the meter 130. Universal coding saves the cost of replacing the meter 130 by allowing it to be used on many different test strip containers 110. In addition, universal coded strips 120 can be tightly controlled such that many strip lots have the same code and are sorted to fit the meter's fixed code assignment. This method is not technique dependent and helps prevent errors due to mixed strip lots. Furthermore, universal coding always has the correct code such that there is no miss-match between the meter 130 and the strip lot code. However, the narrow limits imposed by this method make this an expensive solution as large amounts of waste are generated during the current manufacturing processes.

Accordingly, there is a need for diagnostic testing systems that are convenient to carry and that minimize the chance that a user will use a diagnostic meter with test media from a brand or lot for which the meter has not been calibrated.

SUMMARY

The present invention meets these and other needs by providing a system for diagnostic testing having a meter for performing a diagnostic test on a sample applied to a test media, a container configured to contain test media compatible with the meter, wherein the meter includes a closure portion for selectively closing the opening of the container. In addition, the container may include a light emitting diode (LED) that automatically or selectively illuminates the contents of the container when it is opened. The present invention further provides a sampling device, such as a lancet, operable connected to the container such that that a user may use the sampling device to obtain a sample without disconnecting the sampling device from the container.

The present invention further provides a means for removing a meter from an interconnected test container and reattaching it to a new container using one of several coding methods that transfer lot specific code information from the new container of strips to the meter.

The present invention also provides mechanisms to disable a power source, an auto-on function of the meter, a diagnostic testing function of the meter or other function of the meter when it has been determined that a triggering event has occurred. The triggering event may be, e.g., the expiration of a certain time period, passage of a certain date, performance of a certain quantity of diagnostic tests, or use of a certain quantity of test media. The present invention further provides mechanisms to reconfigure the meter to perform a new function when it has been determined that the triggering event has occurred.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

1. The Integrated System

Figure 1:
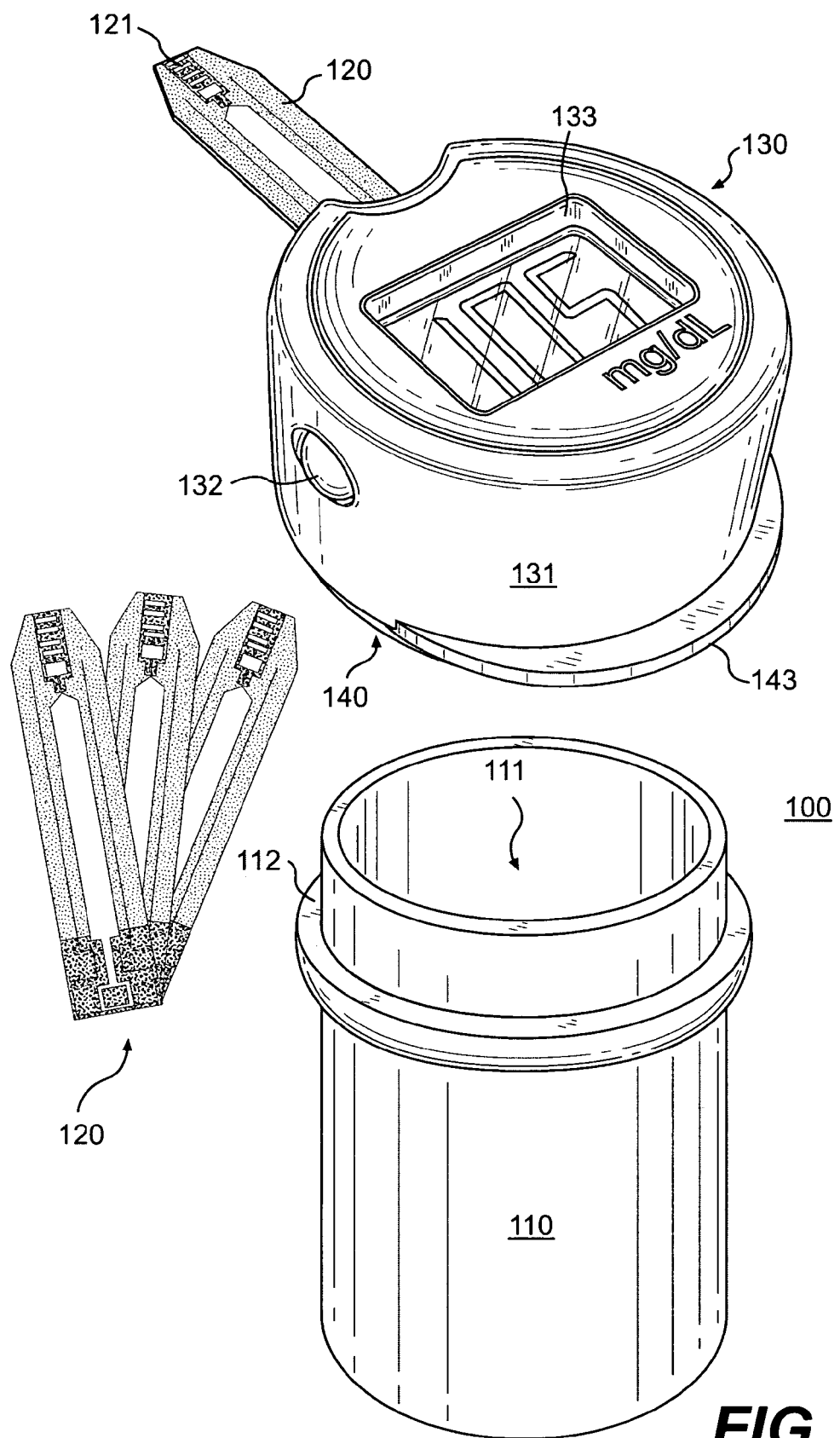
FIG. 1 is a perspective view of a first embodiment of an integrated system consistent with the present invention.

FIG. 1 shows an integrated system 100 for conducting a diagnostic test in accordance with an exemplary embodiment of the present invention. Exemplary integrated system 100 includes a container 110 for containing test media, such as test strips 120, and a meter 130 for performing a diagnostic test using the test strips 120 contained in container 110.

In one illustrative embodiment, the diagnostic test is the determination of the amount of glucose in a sample of whole blood applied to a sample chamber 121 of test strip 120. For blood glucose testing, meter 130 may employ any of a variety of techniques. Preferably, the diagnostic test employs an electrochemical technique (e.g., coulometry, amperometry, potentiometry, etc.). Exemplary electrochemical systems are described in prior U.S. Pat. No. 6,743,635, issued Jun. 1, 2004, and U.S. Pat. No. 6,946,299, issued Sep. 20, 2005, both entitled "SYSTEM AND METHOD FOR BLOOD GLUCOSE TESTING" and both having assignee in common with the instant application, which are incorporated by reference herein in their entirety. Alternatively, meter 130 may employ a photometric technique (e.g., reflection, transmission, scattering, absorption, fluorescence, electro-chemiluminescence, etc.) to determine the amount of glucose in the sample. Exemplary photometric systems are described in U.S. Pat. Nos. 6,201,607, 6,284,550 and 6,541,266, each having assignee in common with the instant application, which are incorporated by reference herein in their entirety. However, electrochemical techniques are currently preferred because, among other reasons, they require a smaller blood sample (on the order of 1 µL or less) than the photometric techniques (on the order of 1 µL or greater). Further, the instrumentation for the electrochemical techniques typically requires less power and can typically be made more compactly than the instrumentation for the photometric techniques.

Integrated system 100 will be illustrated with reference to a diagnostic test to determine the concentration of blood glucose using an electrochemical technique, with the understanding that the principles of the present invention are equally applicable to other types of diagnostic tests and techniques, such as those mentioned above. Further, although the present invention has been illustrated as utilizing test media in the form of test strips 120, exemplary embodiments of the present invention are not limited to a particular type of media and those of skill in the art will recognize that the principles of the present invention are equally applicable to diagnostic testing systems which employ test media in other forms, e.g., tabs, discs, etc.

Figure 6:
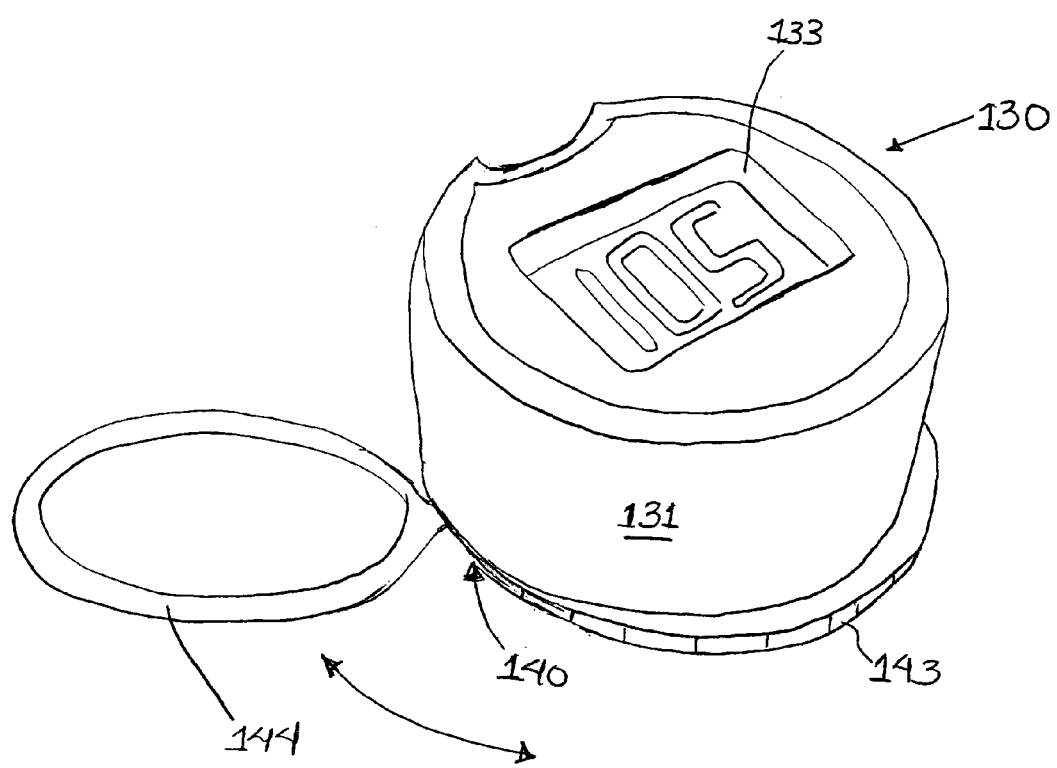
FIG. 6 is a perspective view of a meter housing comprising a holder configured to receive one or more devices used for diagnostic testing.

Meter 130 may be contained within a housing 131. The meter housing 131 is attached to or otherwise includes a closure portion 140 (bottom of meter 130 in FIG. 1) which engages container 110 in order to selectively close an opening 111 of the container. Meter housing 131 may additionally include a holder 144 that is configured to receive one or more containers 110, as illustrated in FIG. 6. Holder 144 is configured to be stored underneath closure 140 when not in use and is slidably movable (as illustrated by the position arrow) to a side position of the container 110 in order to receive and hold additional containers 110. Opening 111 may be the only opening in the container 110. In an illustrative embodiment, meter housing 131 has one side (e.g., the bottom of meter housing 131 in FIG. 1) which is shaped to conform to the closure 140 and is affixed to the closure 140, e.g., by a mechanical attachment (clips, etc.), bonding, gluing, welding, etc. Alternatively, closure portion 140 may be formed integrally with the meter housing 131. The meter 130 and closure 140 together thus form a cap or lid for the container 110.

The closure 140 may be configured to engage the container in a number of ways. In the closed position (see FIG. 3), closure 140 closes opening 111 sufficiently to prevent loss or removal of the test media from container 110. Accordingly, closure 140 is configured to engage container 110 so as to prevent test strips 120 from passing through opening 111 when closure 140 is in the closed position. Container 110 and closure 140 may also be configured to prevent the infiltration of light, liquid, vapor, and/or air into the container so as to prevent contamination or degradation of the test media. Where the test media is configured such that it is toxic or may present a choking hazard, closure 140 may optionally be configured to be child-resistant in order to prevent children from opening container 110 and accessing the test media. For example, closure 140 and container 110 may be configured in a manner similar to well known child-resistant containers for pharmaceuticals or household chemicals.

Figure 2:
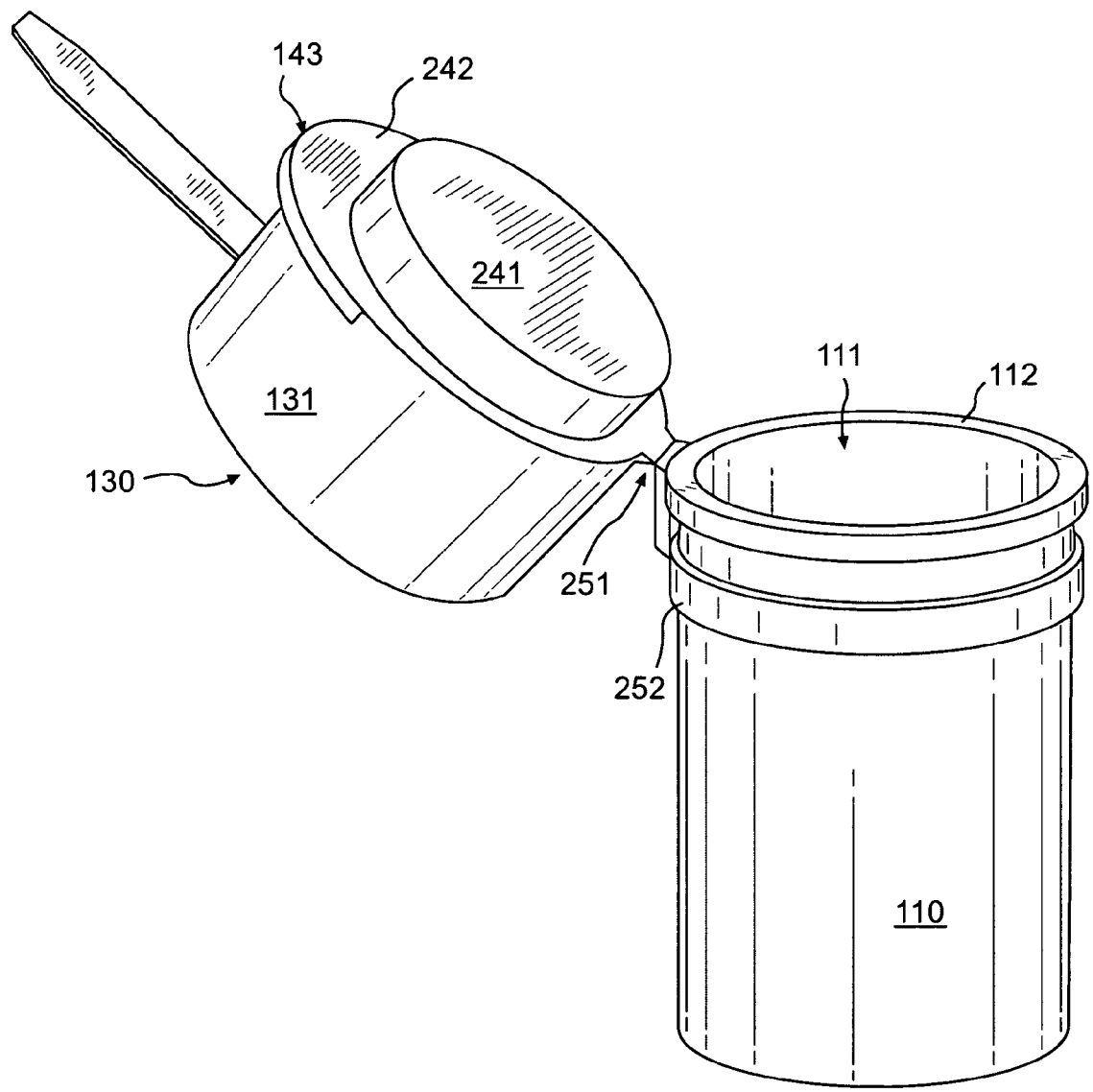
FIG. 2 is a perspective view of a second embodiment of an integrated system consistent with the present invention.

Closure 140 may be configured as a twist-off cap, e.g., by providing inter-engaging threads (not shown) on the closure 140 and the container 110. Alternatively, closure 140 may be configured to slide over the opening, e.g., within grooves (not shown) beside the opening. As a further alternative, closure 140 may be provided with a catch (not shown), such as a detent, that engages container 110 (or vice versa). The catch may be released by a button. However, in an illustrative embodiment, the closure 140 is configured to form a press-fit seal with the container so as to seal the opening against the infiltration of light, liquid and vapor. For example, in FIG. 1, closure 140 is configured with a recess (not shown) to press-fit to the outside of the opening 111, so that the rim of the opening 111 fits within the closure portion 140. Alternatively, closure 140 may be configured with a projection 241 shaped to engage the inside of the opening 111, as shown in FIG. 2. However, it will be understood that the present invention is not limited to any particular configuration of the container and closure and that other configurations may be employed consistent with the principles of the present invention.

For ease of manufacture, opening 111 may be made in the same shape as the container 110. The housing 131 of meter 130 is likewise preferably have an exterior shape similar to that of the container 110 so that the integrated system may be more comfortably held and carried, e.g., in a user's pocket. However, it will be understood that the container 110, meter 130 and opening 111 need not be of the same exterior shape, and the container and meter may be configured in different shapes without departing from the scope of the present invention.

Preferably, the container 110 is generally a right circular cylinder and opening 111 has a circular shape as shown in FIGS. 1 and 2. A circular shape is one possible configuration for the opening because it allows a uniformly tight seal to be formed with a press-fit between the closure portion 140 and the container 110. As shows in FIGS. 1-3, meter 130 may also be generally circular and cylindrical and have a width similar to the width of the container so that the integrated meter 100 has an overall generally circular-cylindrical shape that is comfortable to hold and to carry, e.g., in a pants pocket. However, the container 110, meter 130 and opening 111 may be made in any of a number of other shapes. For example, the container may formed as a right oval, elliptical or rectangular cylinder in order to better conform to a user's shirt pocket.

Figure 3:
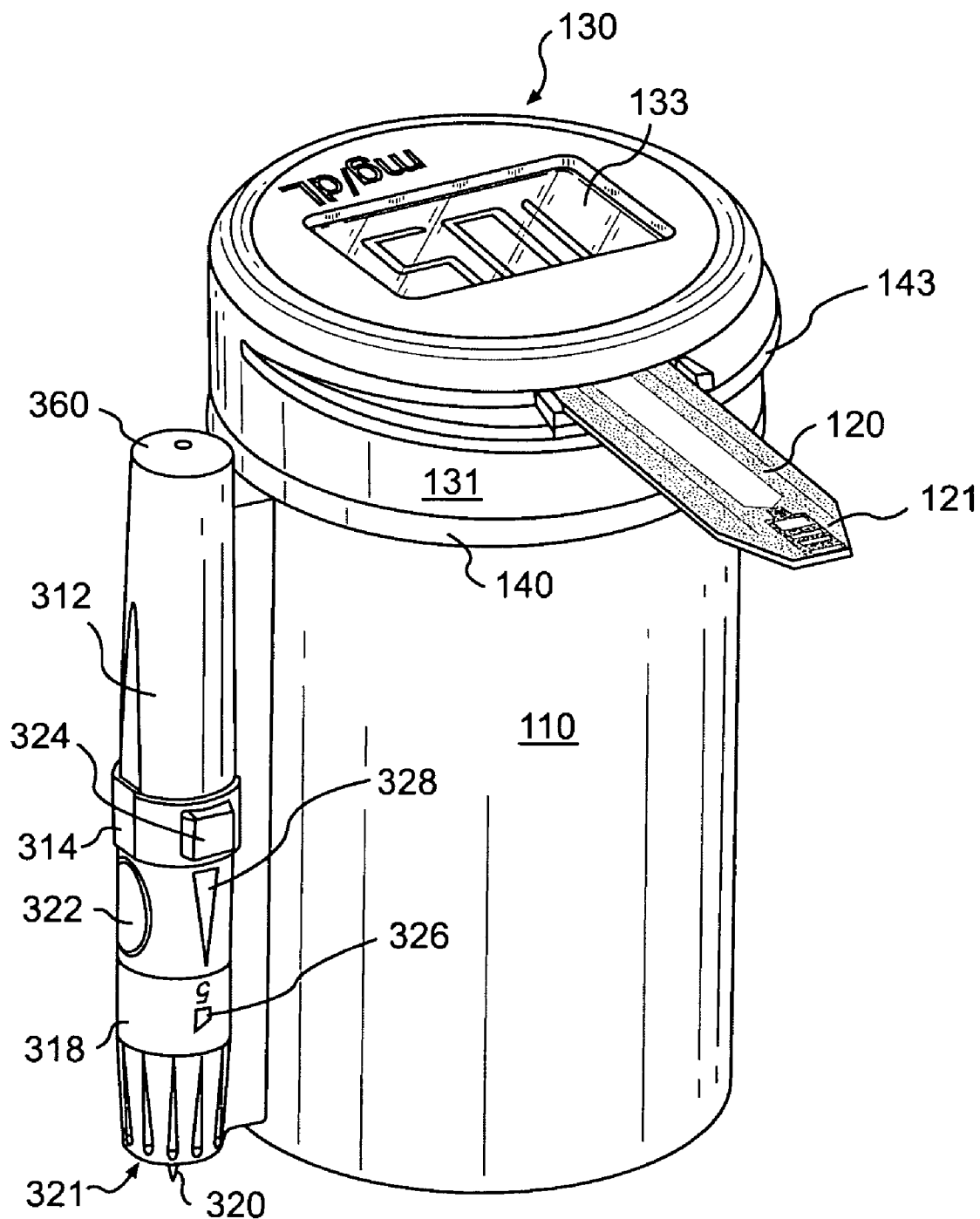
FIG. 3 is a perspective view of a third embodiment of an integrated system consistent with the present invention.

Container 110 and closure 140 may also be provided with corresponding flanges 112 and 242, respectively, that fit flush against each other when the closure portion is in the closed position in order to further prevent the infiltration of liquid and vapor. Closure 140 is also preferably provided with a protrusion 143 which extends beyond the side of container 110 sufficiently to aid to the user in opening and closing the container 110, e.g., by pushing upward with the thumb against the protrusion 143. Protrusion 143 may be an extension of the flange 242, as shown in FIG. 2. Alternatively, protrusion 143 may be formed directly on meter housing 131, as shown in FIG. 3.

Figure 7:
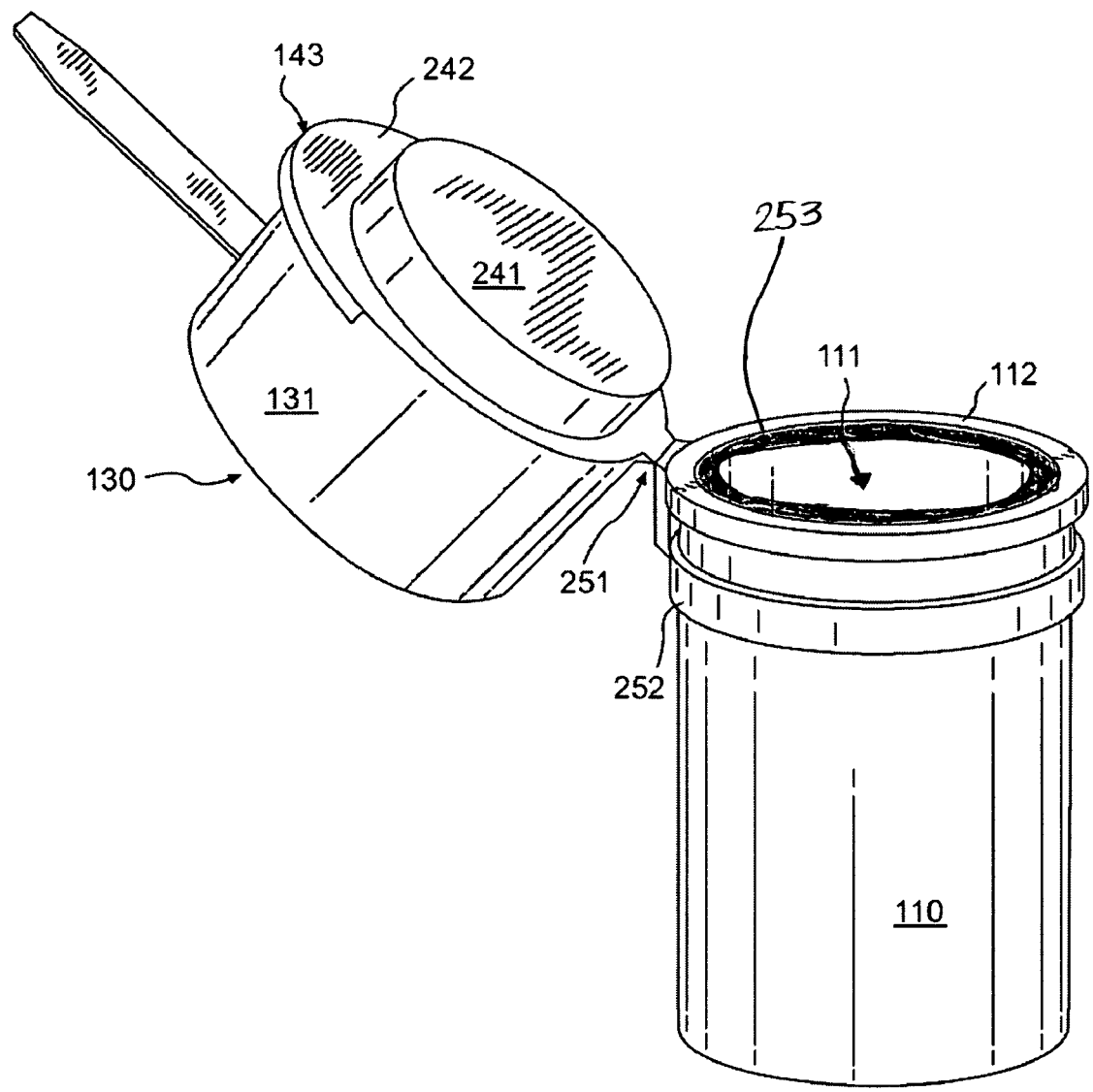
FIG. 7 is a perspective view of a container with a light emitting diode located on the container.
Figure 8:
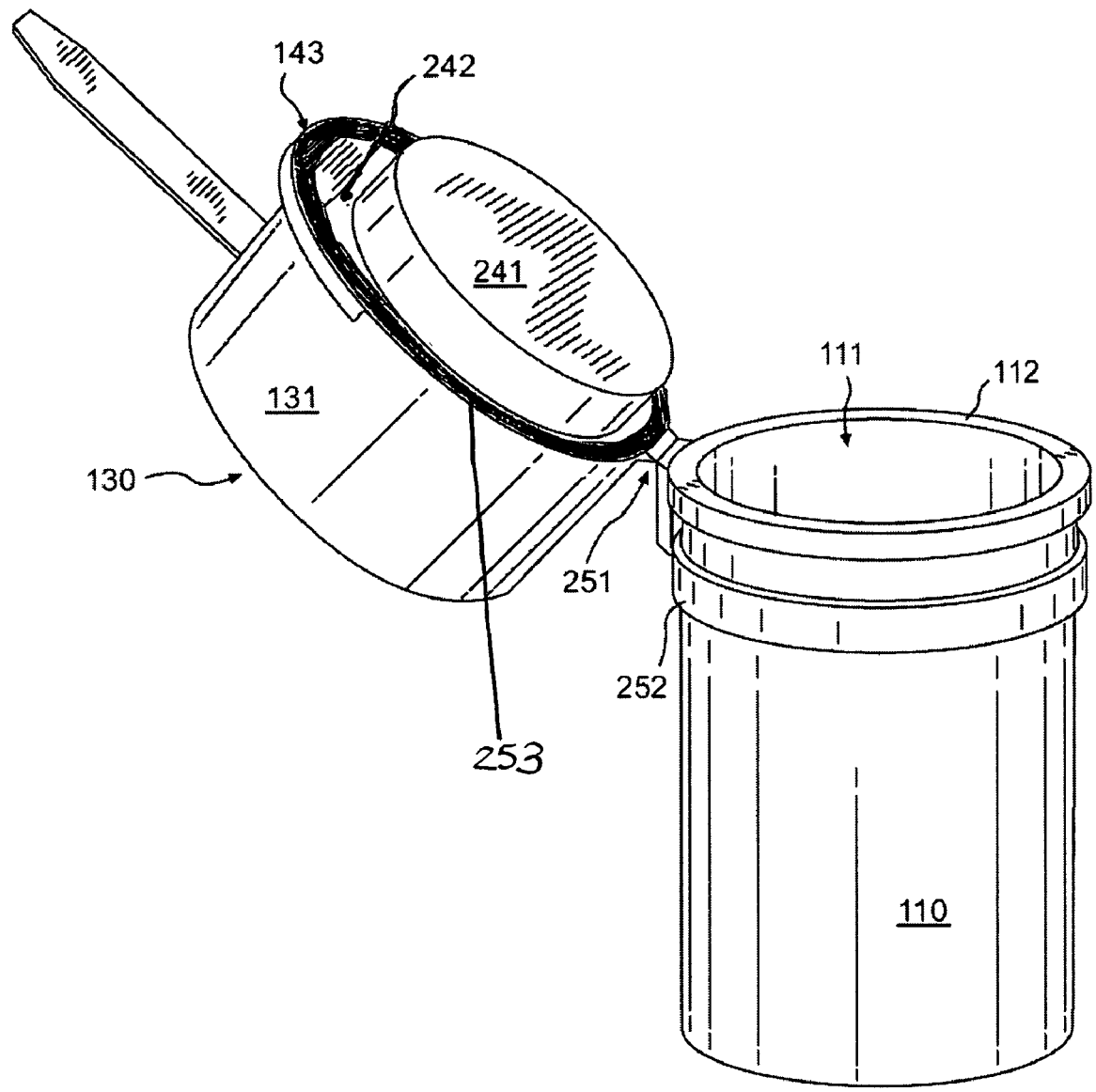
FIG. 8 is a perspective view of a container with a light emitting diode located on the meter.
Figure 9:
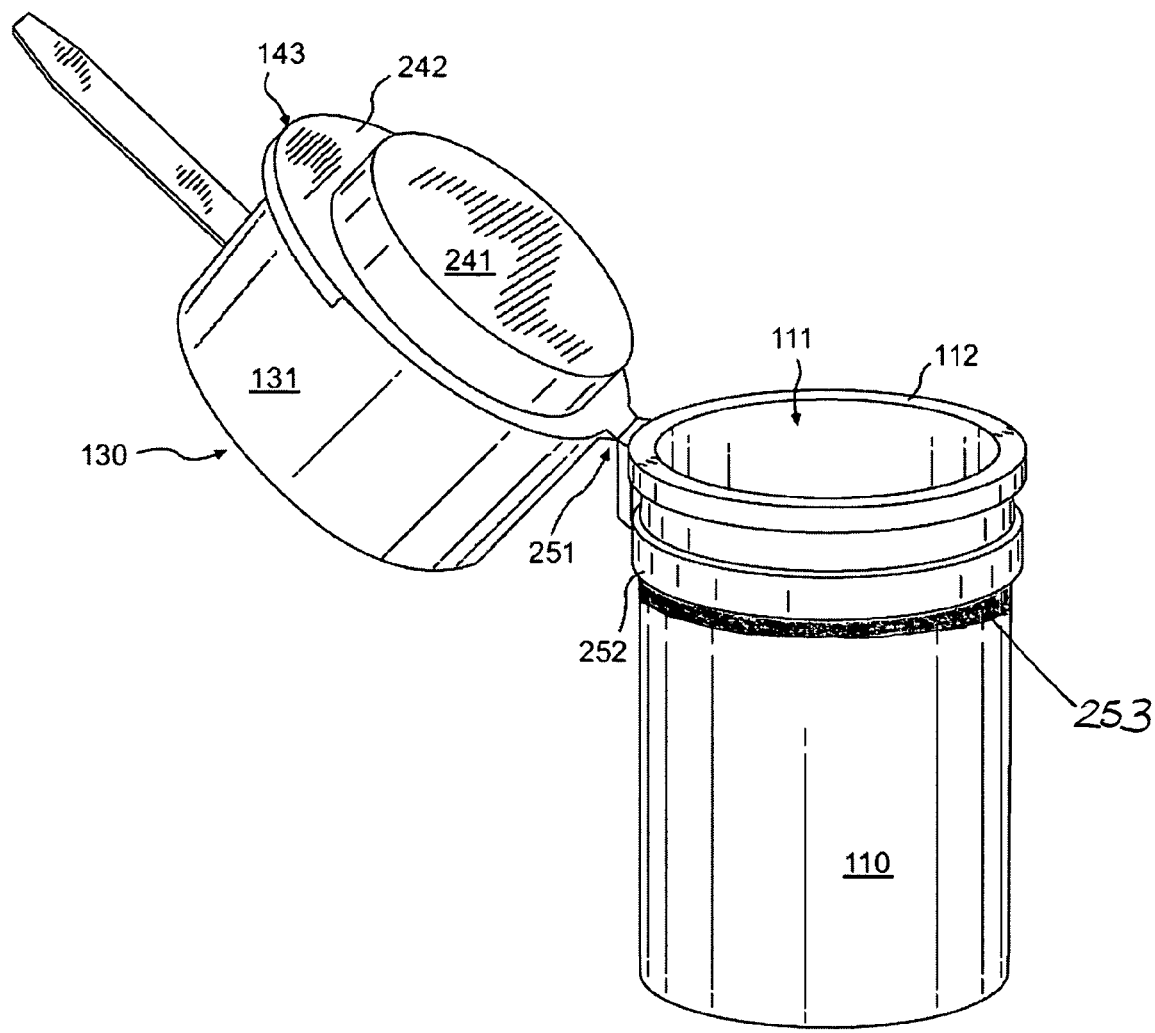
FIG. 9 is a perspective view of a container with a light emitting diode positioned additionally to illuminate an exterior portion of the container.
Figure 10:
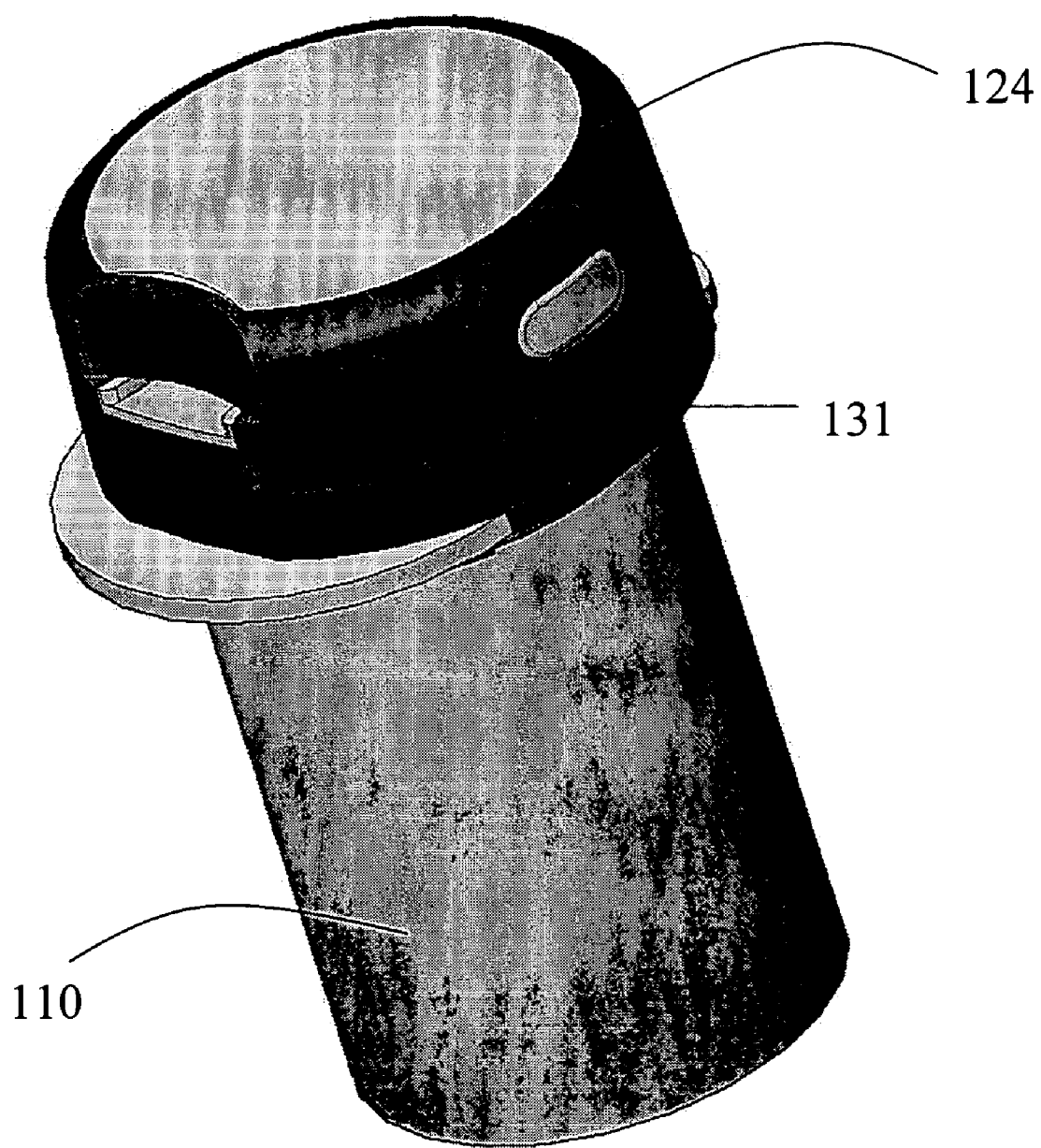
FIG. 10 is a perspective view of a closed container with an illuminated housing.
Figure 11:
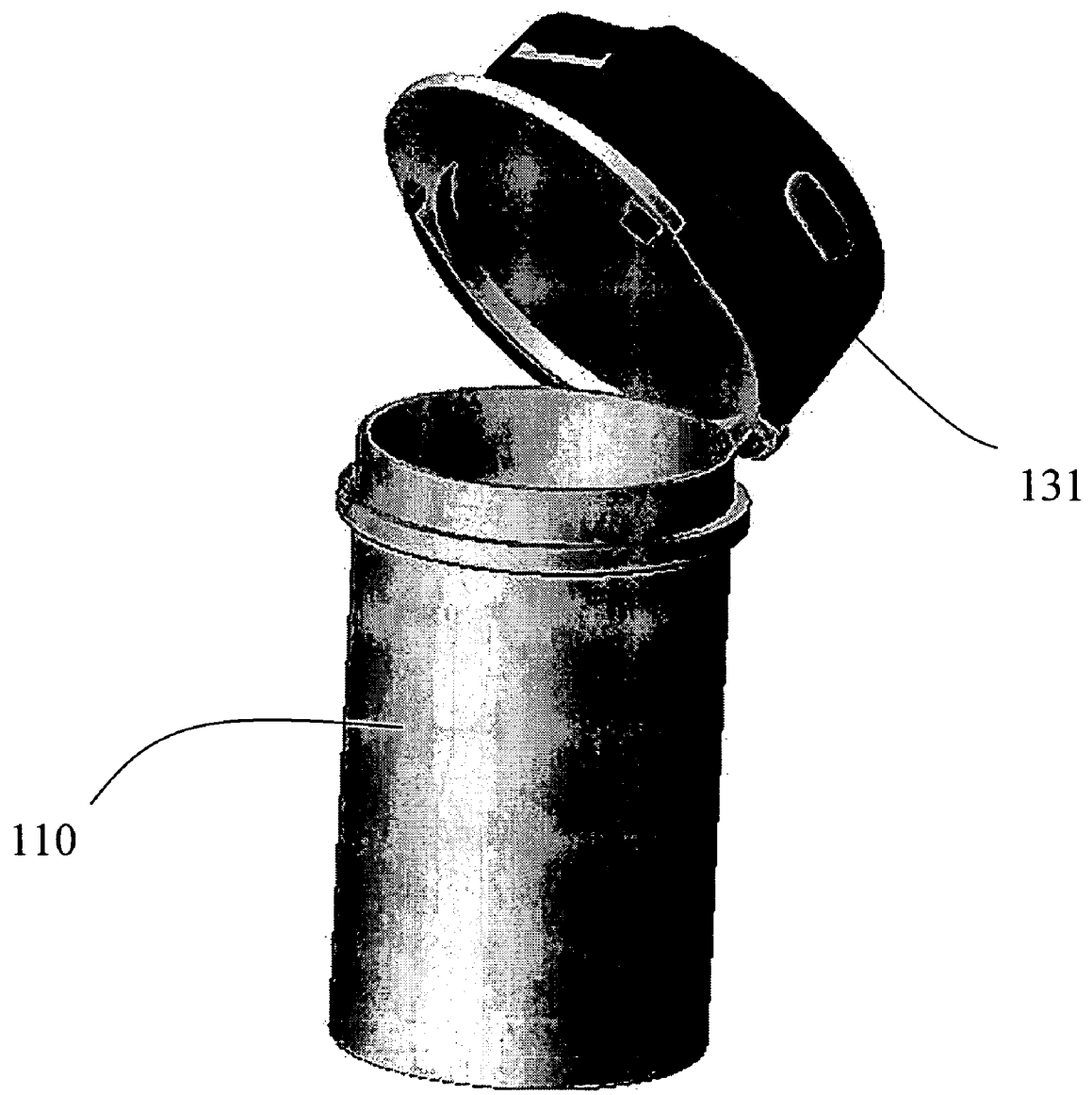
FIG. 11 is a perspective view of an open container with an illuminated housing.

As shown in FIG. 1, container 110 may be opened by completely removing meter 130 and closure portion 140 from the container 110. Alternatively, meter 130 and/or closure 140 may be connected to container 110 in order to prevent the meter 130 from becoming separated from the container. Container 110 and meter 130 may be connected by, e.g., a hinge, lanyard or other flexible connector, such as a flexible plastic band or wire, etc. (not shown). In an illustrative embodiment, a hinge 251 connects the container 110 and the meter housing 131 and/or closure 140. Hinge 251 is positioned such that projection 241 fits within opening 111 in the closed position. The connector (e.g., hinge 251) may have one end connected to the container 110 and the other end connected to the closure 140 and/or meter housing 131. For example, container 110 and closure 140 may be integrally connected by a hinge, e.g., as shown in U.S. Pat. No. 5,723,085, entitled "PROCESS AND APPARATUS FOR MAKING A LEAK PROOF CAP AND BODY ASSEMBLY," which is incorporated by reference herein in its entirety. Alternatively, one end of the connector (e.g., hinge 251) may be connected to a ring 252 that is sized to fit over container 110, as shown in FIG. 2. Ring 252 may be configured to loosely frictionally engage container 110. As another alternative, ring 252 may be affixed to the container 110, e.g., by welding, gluing, etc. In addition, the container 110 may include a light emitting diode (LED) 253 that automatically or selectively illuminates the contents of the container 110 when it is opened. The LED 253 may positioned on the container 110, on the meter housing 131, or positioned additionally to illuminate an exterior portion of the container 110, as illustrated in FIGS. 7-9.

In an exemplary embodiment, container 110 and closure 140 are formed of polypropylene using an injection molding process. However, other materials and processes may be used without departing from the scope of the present invention.

Integrated system 100 may further include a sampling device which the user may use to obtain a sample for testing. The sampling device may be adapted to obtain a biological sample. For instance, the sampling device may be a lancing device that the user may use to draw blood, e.g., for a diagnostic test of blood glucose level.

An exemplary integrated system incorporating a lancing device 360 is shown in FIG. 3. Exemplary lancing device 360 includes a rearward body 312, a finger cover 314, an exterior nozzle 318, an interior nozzle 322 and a trigger 324. Exemplary lancing device 360 further includes an internal spring (not shown) that is used to propel lancet 320 beyond contact surface 321 and through the skin to depth selected by the user.

Figure 18:
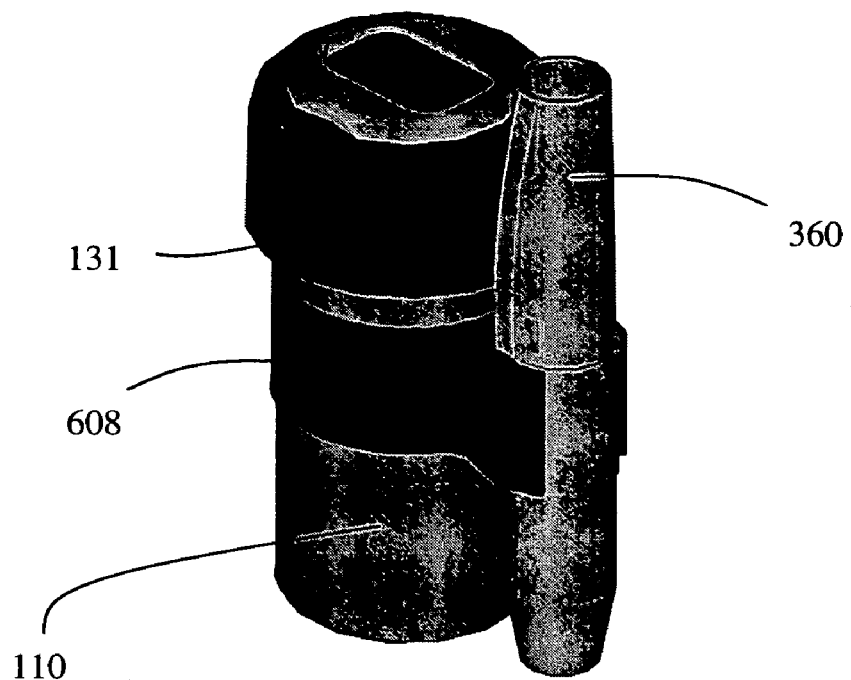
FIG. 18 is a perspective view of a holder in the form of a clip placed around a container.
Figure 18:
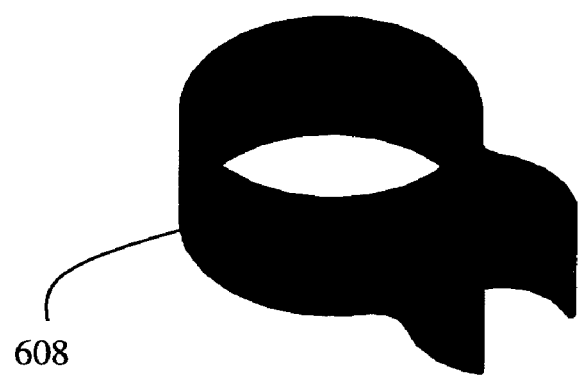
Figure 19:
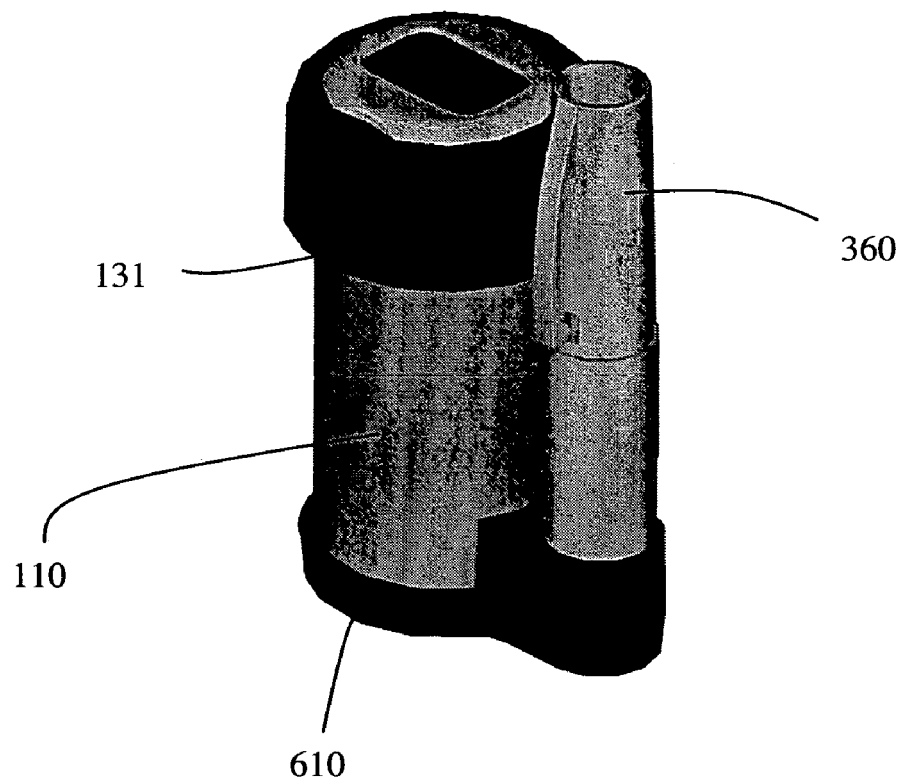
FIG. 19 is a perspective view of a holder in the form of holes used to contain a container and a lancing device.
Figure 19:
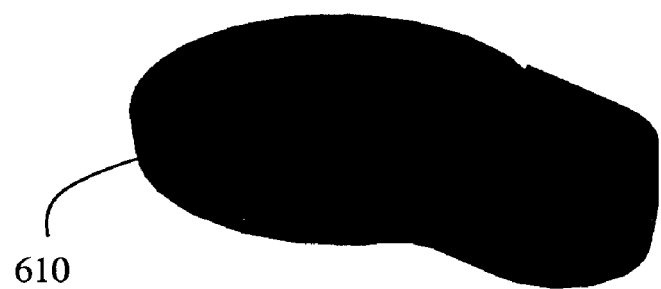

As shown in FIG. 3, the exemplary lancing device 360 is connected to container 110. Lancing device 360 may be permanently connected to the container, for instance, by forming, e.g., rearward body 312, finger cover 314, exterior nozzle 318 or interior nozzle 322 integrally with the container 110, or by bonding one of these components to the container 110, e.g., by a mechanical attachment (clips, brackets, tabs, slots), bonding, gluing, and welding. As would be apparent to one of ordinary skill in the art, other known expedients can be used. Alternatively, lancing device 360 may be releasably connected to the container 110 by providing corresponding releasable connectors on lancing device 360 and container 110. For example, lancing device 360 may be provided with one or more slots, holes, cavities, enclosures, or clips that engage corresponding structures on container 110, or vice versa. As illustrated in FIG. 18, a holder clip 608 can be stretched over container 110 for a snug fit. Holder clip 608 includes a clip that can releasably engage lancing device 360 in place. Similarly, FIG. 19 embodies holder holes 610 designed to engage the container 110 and the lancing device 360 together on one attachment. One having ordinary skill in the art will understand that other types of holders can be used to receive one or more devices used for diagnostic testing, such as brackets, magnets, bayonet locks, slots, tabs, hook and loop fasteners, etc. As further alternatives, lancing device 360 may be connected to housing 131 of meter 130, or to closure portion 140. Preferably only one of the rearward body 312, finger cover 314, exterior nozzle 318 or interior nozzle 322 is connected to the container 110 so that lancing device 360 may be adjusted and used without disconnecting it from the container 110.

In order to draw a sample using exemplary lancing device 360, the user may first select a desired depth of penetration of lancet 320 by rotating exterior nozzle 318 so that the desired depth indicator 326 on exterior nozzle 318 is aligned with arrow 328 on interior nozzle 322. Next, the user loads the internal spring by pulling interior nozzle 322 away from rearward body 312 and places contact surface 321 against the surface to be lanced. The user may then actuate trigger 324 to release the internal spring, which propels lancet 320 beyond contact surface 321 to the indicated depth, and thus into the skin. A blood sample can then be applied to the sample chamber 121 of test strip 120.

Further details of exemplary lancing device 360 are shown in prior application Ser. No. 10/757,776, entitled "LANCING DEVICE," filed Jan. 15, 2004, having assignee in common with the instant application, which is incorporated by reference herein in its entirety. However, the present invention is not limited to any particular sampling device, and one of skill in the art will recognize that other sampling devices can be incorporated in a manner similar to the exemplary lancing device described above.

2. Meter Electronics

Figure 4:
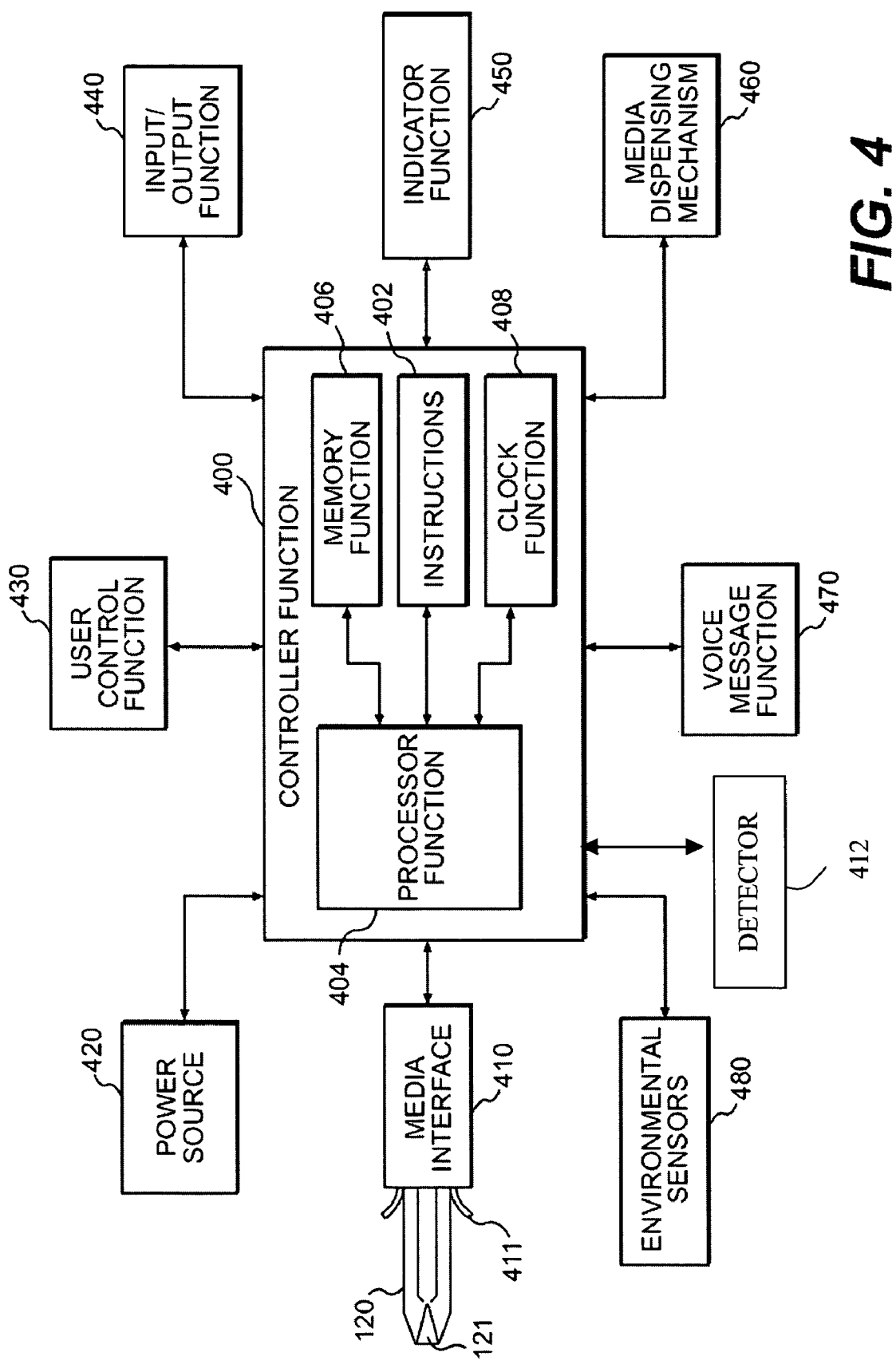
FIG. 4 is a block diagram illustrating the functional components of a diagnostic meter consistent with the present invention.

FIG. 4 shows is a block diagram illustrating functional components of exemplary meter 130. As shown in FIG. 4, meter 130 may include controller function 400, media interface 410, power source 420, user control function 430, input/output function 440, indicator function 450, media dispensing mechanism 460, voice message function 470, and environmental sensors 480. In an illustrative embodiment, the functional components of meter 130 are contained within meter housing 131. However, it will be understood that some or all of the components of a given function may be located elsewhere in integrated system 100.

Controller 400 controls the operation of the functional components of the meter in accordance with its instructions 402, which may be provided as software or firmware. Controller 400 may include processor 404, memory 406, and clock 408 functions. In an illustrative embodiment of the invention, the processor 404, memory 406, and/or clock 408 functions may be implemented using an Application Specific Integrated Circuit (ASIC), which allows controller 400 to be reduced in size in comparison to standard integrated circuit technology. However, it will be understood that the controller may be implemented using standard integrated circuit technology, or other technology, without departing from the scope of the present invention.

Processor function 404 executes instructions 402 used to control the functional components 410-480 of meter 130. In particular, processor 404 executes instructions 402 necessary to perform the diagnostic test (e.g., as set forth in U.S. Pat. Nos. 6,743,635 and 6,946,299, incorporated by reference above). The instructions 402 for the processor 404 may be stored in memory 406 or elsewhere. Memory function 406 may also store data, such as calibration data and other data used in the performance of the diagnostic test. In exemplary embodiments of the present invention, memory 406 is used to store results of the diagnostic test, together with a time/date data and/or associated voice message, for later review or uploading (discussed below).

Clock function 408 regulates the processor's execution of the instructions 402 in time. In particular, clock function 408 is used to regulate the timing of steps in the diagnostic test. For instance, processor 404 may use clock 408 to regulate an incubation time period, or other time periods, necessary for the correct performance of the diagnostic test (e.g., as set forth in U.S. Pat. Nos. 6,743,635 and 6,946,299, incorporated by reference above). Clock function 408 may be implemented by a single system clock or by multiple clocks for different purposes.

Media interface 410 accepts test media, such as test strips 120, for testing and includes a channel 411 to ensure that the test media is correctly positioned when inserted by a user or media dispensing mechanism 460. Interface 410 includes one or more media sensors for determining, e.g., whether a test strip 120 has been correctly inserted in the test port 410 (i.e., whether interface side 122 of test strip 120 is properly positioned with respect to the media sensors); whether an adequately-sized sample has been applied to the sample chamber on the sample side 121 of the test strip; and the presence or concentration of analyte in the sample. For meters using electrochemical techniques, the media sensors may include one or more electrical contacts corresponding to electrodes on the interface side 122 of test strip 120. For meters using photometric techniques, at least the presence or concentration of analyte in the sample is determined using an optical sensor, e.g., a LED and corresponding photo-detector.

Power source 420 provides power to the electronic components of meter 130. In an illustrative embodiment, the power source is a lithium coin cell battery. However, other power sources, such as other types of batteries, solar cells, or AC/DC converters may be used without departing from the scope of the present invention. The output of the power source may be regulated, e.g., by a voltage regulator circuit.

User control function 430 may include, for example, one or more buttons, switches, keys or other controls for controlling the functions of meter 130. In an illustrative embodiment, user control function 430 is implemented by one or more buttons 132 placed on the left side of meter housing 131 (see FIG. 1). In this position, button 132 may be comfortably pressed with the right thumb or index finger while the integrated system 100 is held in the right hand, with display 133 in an upright position. However, user control 430 may be positioned elsewhere on meter 130. For example, button 132 may be placed on right hand side of the meter housing 131 in order to be more convenient for left handed users, or on the top of the meter, e.g., centered under display 133. As another example, user control function 430 may include a switch actuated when the user opens the closure 140, e.g., so that the meter 130 automatically turns on when the user opens container 110 to retrieve a test strip.

In an exemplary embodiment of the present invention, user control function 430 is implemented using a single control, e.g., a single button 132, that is used to control a plurality of meter functions. For example, user control 430 may be used to control the input/output 440 function, indicator function 450, media dispensing mechanism 460, and/or voice message function 470 by providing commands to these functions directly or through controller 400. User control 430 may also be used to control the diagnostic test function of controller 400. For example, when a test is to be performed using a control solution (e.g., as set forth in U.S. Pat. Nos. 6,743,635 and 6,946,299, incorporated by reference above), button 132 may be held down to indicate to controller 400 that the current sample is of a control solution and, consequently, that controller 400 should perform a control test on the current strip.

Alternatively, a plurality of user controls, e.g., a plurality of buttons 132, may be provided, with each button having different functions. For example, two buttons may be provided to allow a user to scroll through diagnostic test results stored in memory 406 in either forward or reverse directions. As an aid to the user, the function of the button or buttons 132 at the particular time may be dynamically indicated by indicator function 450. For example, when reviewing previous test results, indicator function 450, e.g., a display 133, may instruct the user to "PRESS BUTTON TO VIEW NEXT RESULT." Further, user controls 430 may have different functions at different times. For example, holding button 132 down upon the insertion of a test strip into media interface 410 may command the controller to perform a control test on that strip, while holding the button down without inserting a test strip may command the controller to display the result of the previous diagnostic test.

Input/output function 440 provides for the downloading of data or instructions 402 to meter 130, and/or the uploading of data from meter 130. Input/output function 440 may be used, for example, to upload the results of a diagnostic test or tests so that they may be transferred to a storage device or to a third party, e.g., a medical care provider for use in treating the user. Alternatively, input/output function 440 may be used to download data (e.g., calibration data) or instructions 402 (e.g., updated software) to the meter 130. Input/output function 440 may be implemented using any conventional digital or analog information interface, e.g., a serial port, a parallel port, an optical port, an infrared interface, etc.

Indicator function 450 indicates the result of the diagnostic test to the user, e.g., as a numerical value together with the units of measurement. In addition to indicating the result of the diagnostic test, the indicator may present other information to the user. For example, the indicator 450 may indicate the average result of a plurality of tests, the time and/or date, remaining battery life, etc. (e.g., as set forth in U.S. Pat. Nos. 6,743,635 and 6,946,299, incorporated by reference above). Indicator 450 may also be used to prompt the user to perform certain steps of the diagnostic test, e.g., to apply the sample to the test strip 120. In an exemplary embodiment of the present invention (discussed below), indicator 450 indicates the number of test strips remaining in container 110, or the number of tests or the time remaining before meter 130 becomes inoperative.

Figure 12:
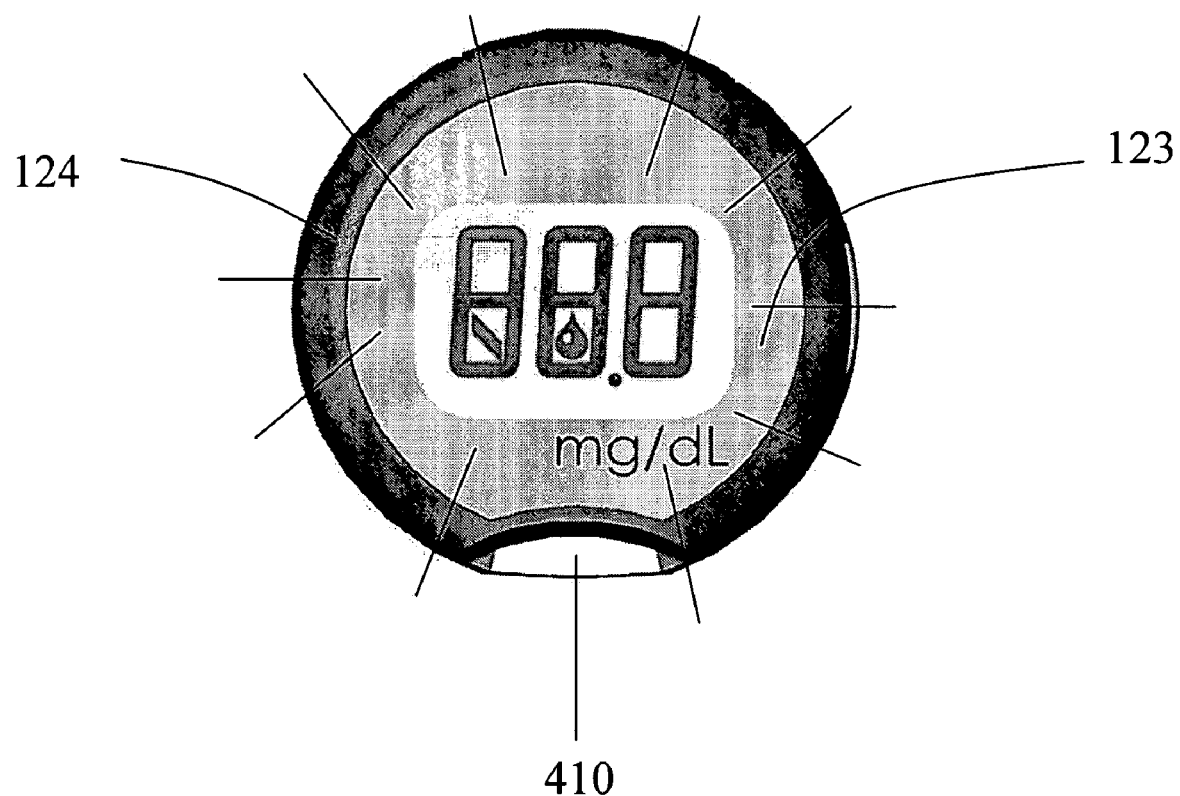
FIG. 12 is a perspective view of a top portion of a container housing comprising a backlit display and a ring-portion.
Figure 13:
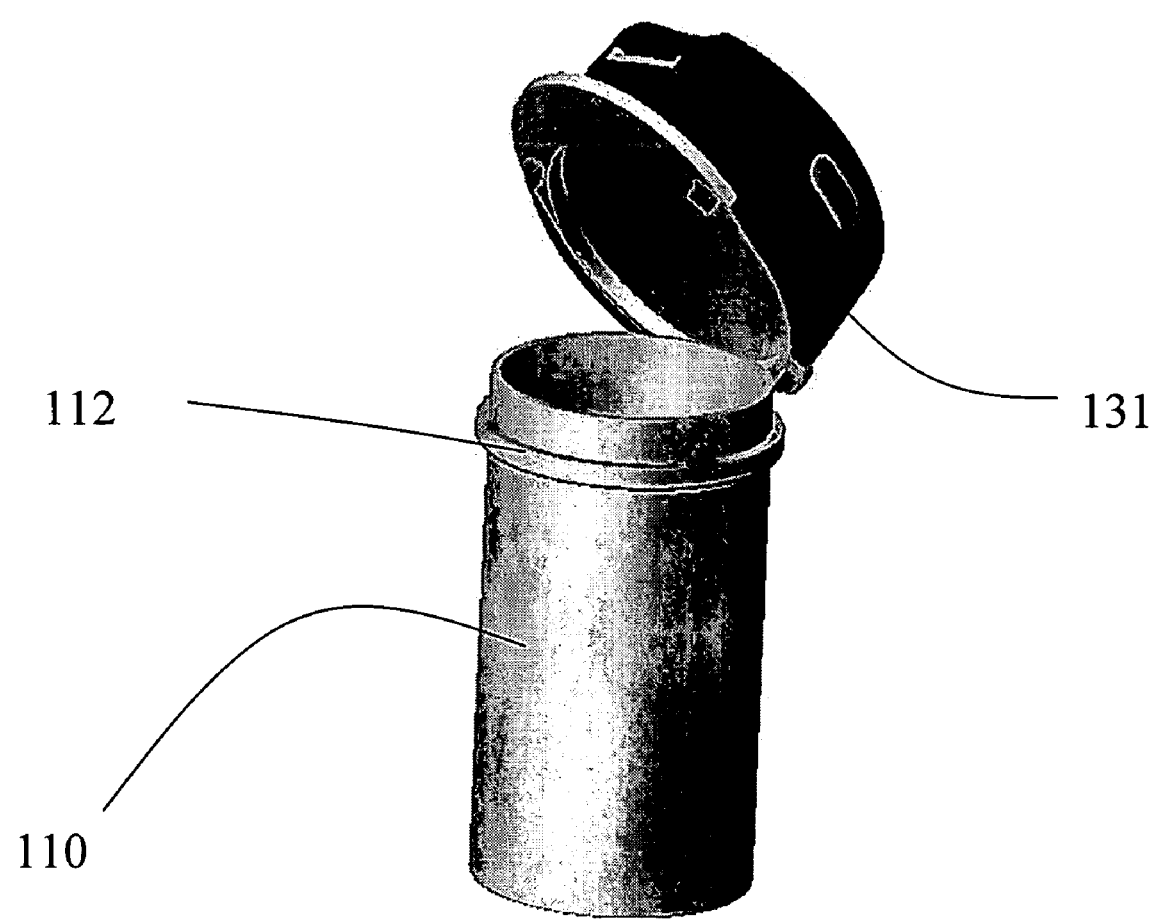
FIG. 13 is a perspective view of an open container with an illuminated flange.

Indicator function 450 may present information in visible, audible or tactile form. For example, indicator 450 may include a display 133 for displaying information, e.g., using numerical values, words and/or icons. A number of different technologies may be used for display 133. For example, the display may be a liquid crystal display, a vacuum fluorescent display, an electroluminescent display, a LED display, a plasma display, etc. In an illustrative embodiment, display 134 is a liquid crystal display. In addition, as illustrated in FIG. 12, indicator function 450 may include a backlit display 123 to light the insertion point of the test strip 120 when it is inserted into test port 410. Furthermore, a top ring-portion 124 of housing 131 can be optically coupled to the backlit display 123 and constructed with a colored transparent molded piece that light-pipes from either the backlight or a vial-light LED 253 (FIGS. 7-9) to improve visibility if the test strip 120 is inserted in a poorly lit area. In addition, as illustrated in FIG. 13, flange 112 is also constructed with a transparent molded piece that lights up as the container 110 is opened.

Alternatively or in addition, indicator 450 may include an audible indicator configured to indicate information by sound. For example, indicator 450 may include a speaker connected to a voice and/or sound circuit that is configured to, e.g., speak the result of the diagnostic test or to beep to indicate that an error has occurred. As a further alternative, indicator 450 may be implemented as a dynamic Braille indicator for use by the blind.

In an illustrative embodiment, indicator function 450 includes a display 133 as well as a speaker connected to a sound circuit (not shown). The display 133 may be placed on the top of meter housing 131 as shown in FIGS. 1 and 3. In this position, display 133 is conveniently visible when the meter is grasped in the hand with the thumb or index finger on button 132.

Because the diagnostic test media, e.g., test strips 120, is typically very small, certain users may find it difficult to retrieve the test media from the container 110. Accordingly, a media dispensing mechanism may be used to provide for the automated dispensing of test media from the container.

Figure 5:
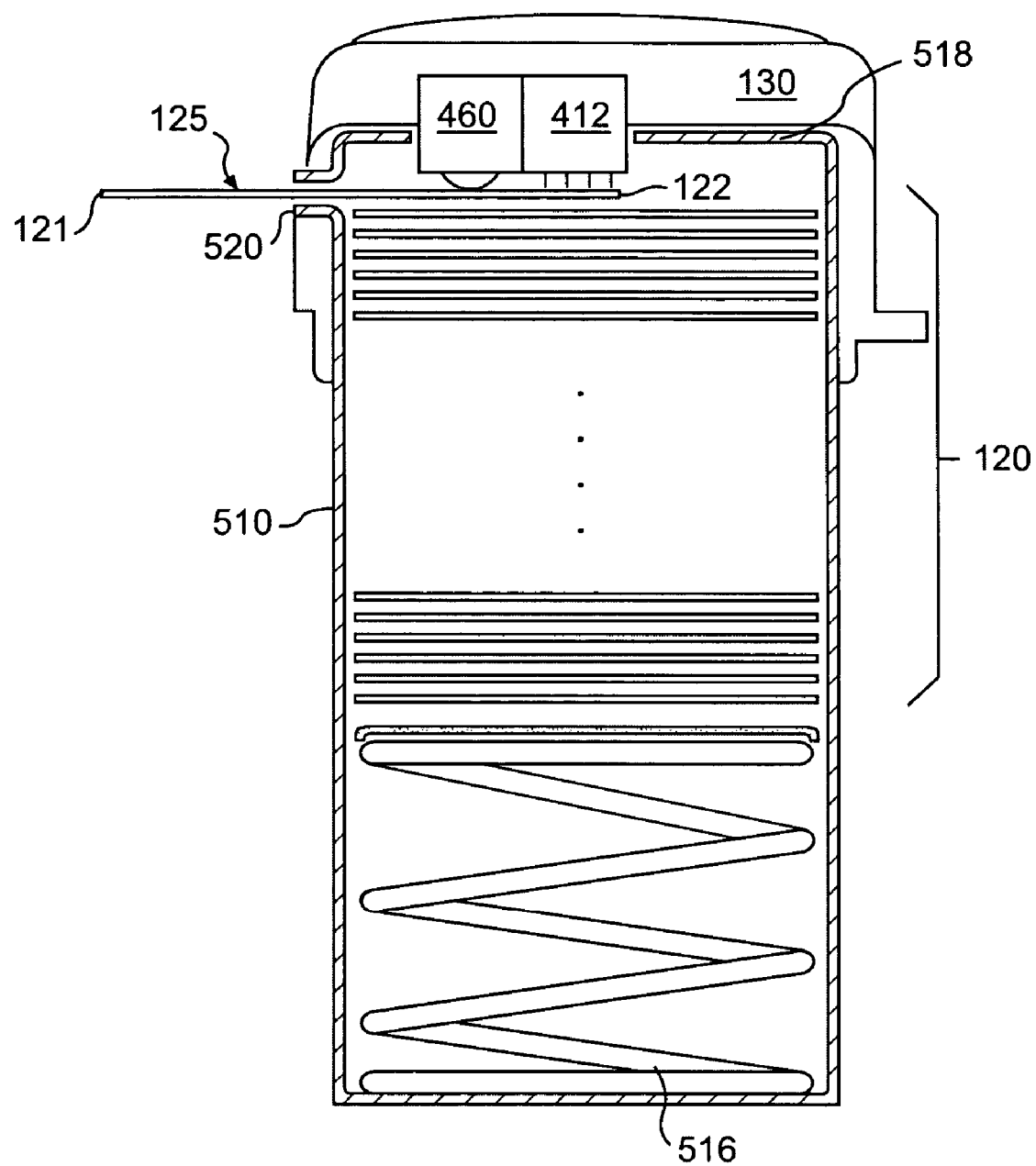
FIG. 5 is a cross-sectional view of an integrated fourth embodiment of an integrated system consistent with the present invention.

FIG. 5 shows a cross-section of an exemplary integrated system having a media dispensing mechanism 460. In this embodiment, the container is configured as a spring-loaded magazine 510. A plurality of test strips 120 are stacked on top of one another in magazine 510. Magazine 510 may have an interior shape similar to that of the test media in order to maintain the alignment of the stack. For example, for the test strips 120 depicted in FIG. 1, the interior of magazine 510 may be generally rectangular in cross-section.

Spring 516 pushes the stack of test strips against the top 518 of magazine 510, where the top test strip 125 is operably positioned with respect to strip dispensing mechanism 460. Dispensing mechanism 460 dispenses the top test strip 125 in the stack using a linear and/or rotational mechanical action. The mechanical action may be executed manually (e.g., by the user pulling a slide or rotating a wheel) or by a motor (e.g., a stepper motor) actuated by user control function 430. The top test strip 125 is slid from the stack and through slot 520.

The test media used with this embodiment may be modified by application of a non-friction coating or film, such as TEFLON, to one or both sides in order to ensure smooth ejection.

Where the particular diagnostic test requires that the test strip be inserted into the media interface 410 before the sample is applied, media dispensing mechanism 460 may position the interface side 122 of the ejected test strip 125 within media interface 410, e.g., with the interface side 122 of the test strip engaging the media sensors and the sample chamber 121 of the test strip projected outwardly from the meter 130 so as to allow application of a sample, as shown in FIG. 5. Alternatively, media dispensing mechanism 460 may simply present either end of the top test strip 125 to the user, who may then manually insert the test strip 125 into media interface 410 (either before or after the sample is applied, depending on the requirements of the particular diagnostic test). Controller 400 may be instructed to count the number of test strips 120 dispensed by media dispensing mechanism 460 and cause indicator function 450 to indicate, e.g., the number of test strips 120 remaining in magazine 510.

Voice message function 470 may be used to record a voice message associated with a given diagnostic test result. For self-testing of blood glucose level, for example, a user may use voice message function 470 to record information related to their diet around the time of the diagnostic test. The voice message may be recorded in memory 406 along with a pointer associating it with a particular test result. The use of the voice message function 470 is more fully explained in prior application Ser. No. 10/764,974, entitled "MEDICAL DIAGNOSTIC TESTING DEVICE WITH VOICE MESSAGE CAPABILITY," filed Jan. 26, 2004, having assignee in common with the present application, which is incorporated by reference herein in its entirety. At the end of the useful life of the meter 130, meter 130 itself may be given or sent to the user's medical care provider. The medical care provider may then review the results of the diagnostic tests and/or associated voice messages for use in treating the user.

Environmental sensing function 480 may include one or more environmental sensors used to gather data used in the performance of the diagnostic test. Such environmental sensors may include, e.g., a temperature sensor and/or a humidity sensor. For example, meter 130 may use a temperature reading to correct the diagnostic test result for temperature dependence (e.g., as set forth in U.S. Pat. Nos. 6,743,635 and 6,946,299, incorporated by reference above). As a further example, meter 130 may use a humidity reading to determine if the humidity level is too high to proceed with the diagnostic test.

3. Prevention of the Use of Incorrect Test Strips

Meter 130 may be calibrated for use with a particular brand or manufacturer's lot of test media by customizing the diagnostic test performed by meter 130 with respect to the particular brand or lot using one or more calibration parameters. These calibration parameters may include environmental corrections (e.g., temperature corrections), timing period corrections (e.g., with respect to incubation time), voltage corrections (e.g., for use in electrochemical tests), color variations (e.g., for use in photometric tests), etc., that customize the diagnostic test function of controller 400 to the particular brand or lot of test media. See, e.g., U.S. Pat. Nos. 6,743,635 and 6,946,299, incorporated by reference above.

In an illustrative embodiment of the present invention, integrated system 100 includes one or more containers 110 or magazines 510 of test strips 120 packaged together with a meter 130. The test strips 120 in the package are from the same manufacturing lot or otherwise have the same characteristic reaction to blood glucose so that meter 130 may be calibrated once and thereafter used with any of the test strips 120 in the package without recalibration.

The diagnostic test function of the packaged meter 130 may be precalibrated by the manufacturer or distributor, e.g., by providing instructions 402 and/or data customized to the associated test media. Alternatively, meter 130 may be calibrated at the user level by requiring the user to calibrate the meter with respect to a particular brand or lot of test media prior to using the meter to conduct diagnostic tests. For example, the user may use the user control 430 or input/output 440 functions to enter or download calibration data or a code from which controller 400 may derive calibration data. In another approach, each test media container 110 (or a co-packaged group of containers from the same lot) may be provided with a data storage device that stores the calibration data electronically. See, e.g., U.S. Pat. Nos. 6,743,635 and 6,946,299, incorporated by reference above.

In the event the test strips 120 in the package are not from the same manufacturing lot or otherwise do not have the same characteristic reaction to blood glucose, users may forget to calibrate the meter 130 for use with a new brand or lot of test media. Accordingly, the present invention allows the meter 130 to be removed from the test strip container 110 and transferred to another container by using several different coding techniques that prevent erroneous results that could have serious consequences for the user if the meter 130 is incorrectly calibrated. As long as the meter is properly associated with a coding container for strips of a matched lot, the user does not need to take further action to program the meter.

In one illustrative embodiment, common coding errors associated with forgetting to change a code chip or button code are prevented by the method of on-strip coding. This method is carried out on the test strip 120 provided to the meter 130. A set lot code parameter that corresponds to the specific test strip lot is selected from the meter's memory 406. On-strip coding is similar to universal coding in that this method is also not technique dependent and saves the cost of disposing the meter 130 with each vial of strips 120.

Figure 14:
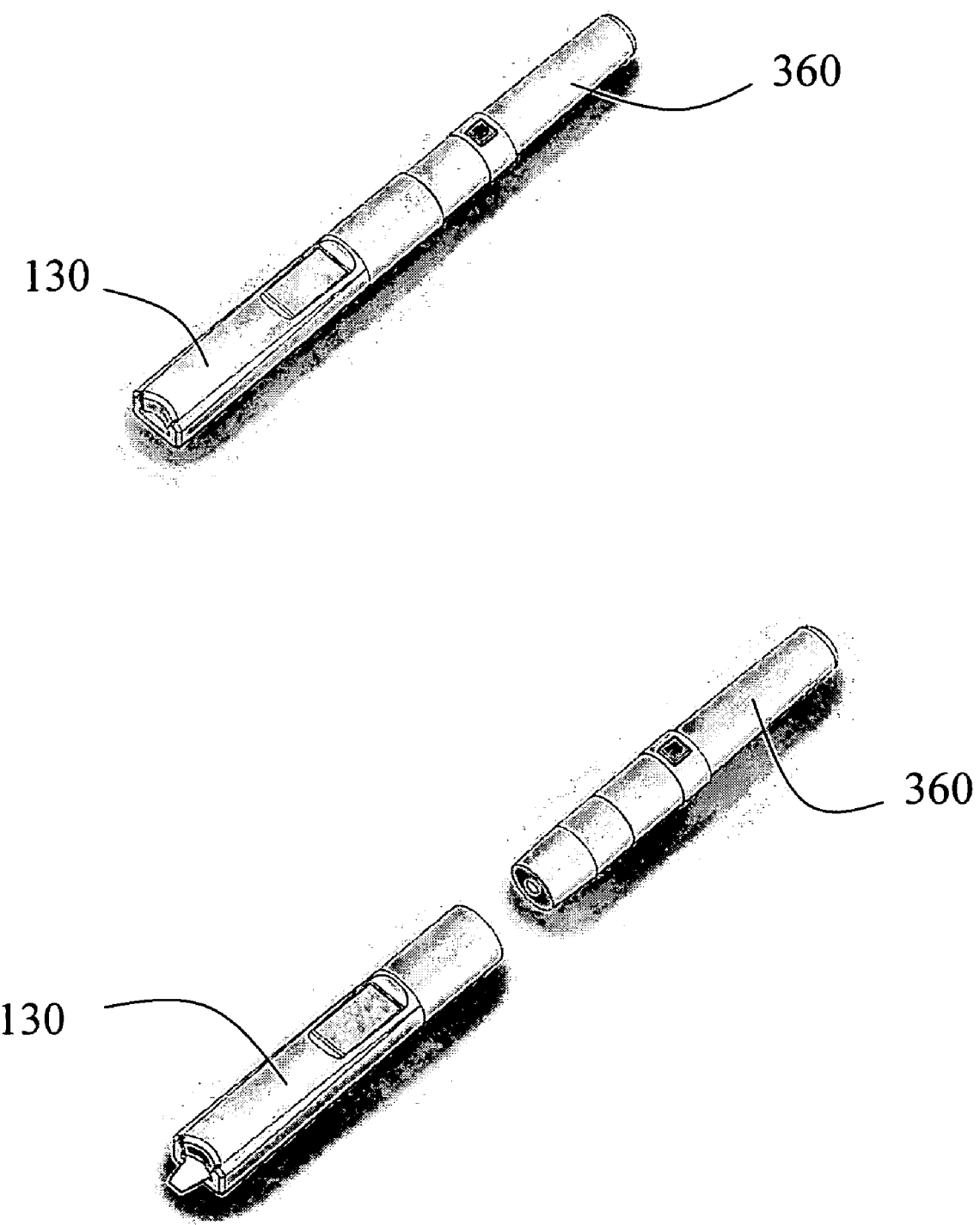
FIG. 14 is a perspective view of a lancing device with a replaceable meter.
Figure 15:
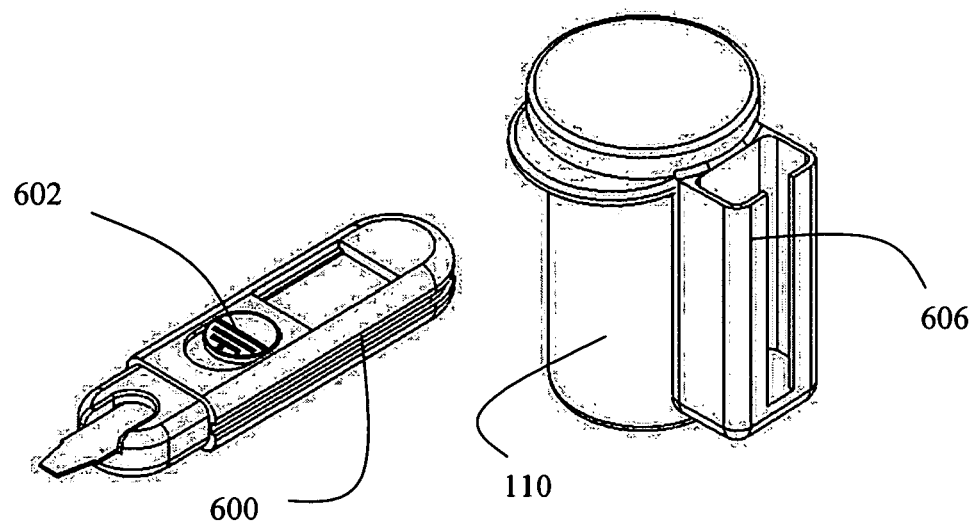
FIG. 15 is a perspective view of a remote meter with on-strip coding and a strip ejector mechanism.
Figure 16:
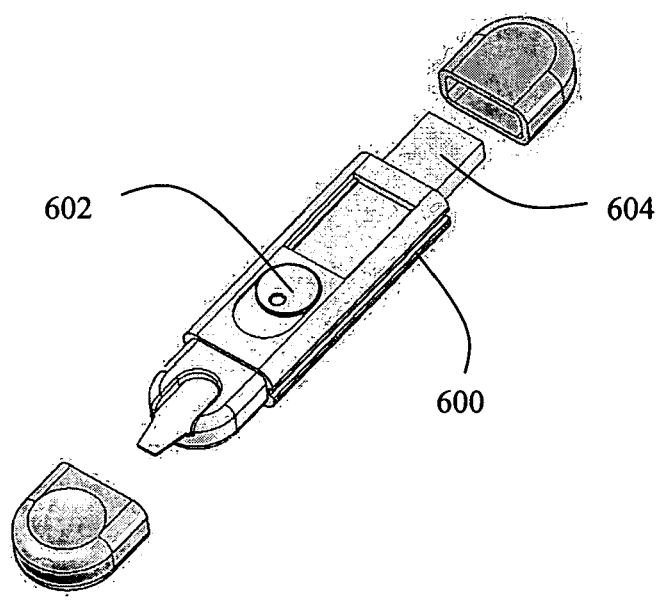
FIG. 16 is a perspective view of a remote meter USB data connecter with on-strip coding and a strip ejector mechanism.

In addition, as illustrated in FIGS. 15 and 16, the reduced size of the test strip 120 may require a meter 130 with a strip ejector mechanism 602 in order to dispose of the strip 120 without touching it. Moreover, a lancing device 360 may be integrated with the meter 130 as shown in FIG. 14.

Another coding method that allows the metering device 130 to be removed from the test strip container 110 and transferred to another container is button coding. A user selects a code number on the meter 130 each time the meter 130 is interconnected to a different container. The user then enters a code that is visually read by the user based on a value printed on the test strip container 110. At least one advantage of using button coding is that it does not require a secondary manufacturing operation to add a code to a test strip 120 after the code is determined for that strip lot. However, this coding method may be less desirable than universal and on-strip coding due to the possibility of coding entry errors by the user.

In an alternative embodiment, code chip coding may also be used as an effective means for calibrating the meter 130. The method of code chip coding requires the user to insert a code chip with lot specific information included in each package of strips 120 into the meter 130. Code chip coding is advantageous in that it provides a means for data storage. However, there is a possibility that the user could confuse old code chips for new ones by mistake, thus causing coding errors. Also, it is also not always space efficient to use code chips due to package and connector size. Moreover, code chip coding requires the user to handle an additional system component for testing than other coding techniques. Nevertheless, code chip coding is a viable coding alternative.

Figure 17:
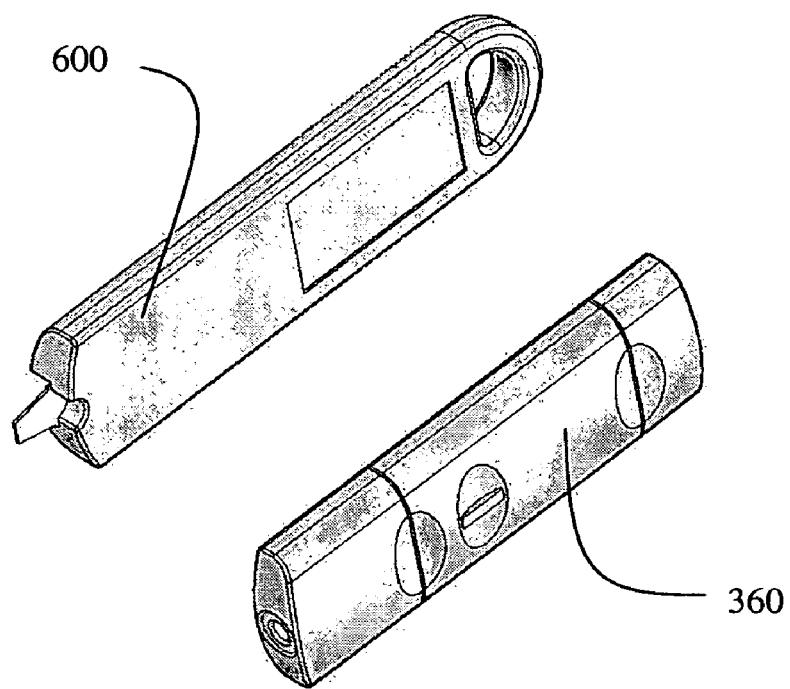
FIG. 17 is a perspective view of a remote meter with on-strip coding and a strip ejector mechanism attached to a lancing device.
Figure 17:
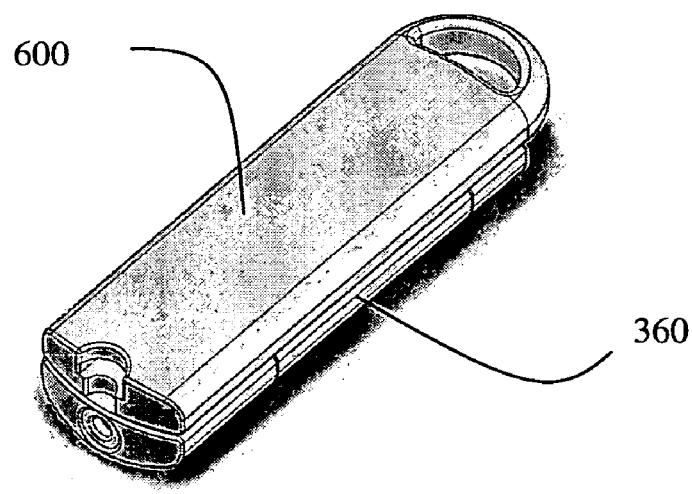

Alternatively, meter 130 may be calibrated by means of a Universal Serial Bus (USB) device 600. Each test media container 110 (or a co-packaged group of containers from the same lot) may be provided with a data storage device 600 that stores the calibration data electronically. To calibrate the meter 130 for the test media in the particular container 110 or package, the user simply plugs the corresponding data storage device 600 into a connector (not shown) on meter 130. The controller 400 then obtains the necessary instructions 402 or data from the data storage device 600. In addition, USB remote meters 600 can transfer data to a personal computer (PC) (not shown) directly from the integral USB data connector 604 (e.g., as set forth in commonly-assigned application Ser. No. 11/118,494 filed May 2, 2005, which is incorporated herein by reference in its entirety). The data connector 604 can also be attached to test strip container 110 via a holster-type receptacle 606 formed on the side of the test strip container 110 (as shown in FIG. 15), providing a convenient form to transfer data directly to the PC. Moreover, this device can be used as an "electronic log book" to transfer stored data in the meter 130 to the PC. The display shows basic results, but date and time can be set via PC and time and date information sent to the PC with each result. In addition, the PC application can be launched after detecting the USB connection to the PC. Alternative embodiments provide a remote meter 600 with on-strip coding and an ejector button 602 attached to a lancing device 360 that can be used together or separately as illustrated in FIGS. 15-17.

Although the coding methods described above are designed to prevent meter calibration errors, the integrated diagnostic test system further employs additional safeguards to minimize the chance that a user will mistakenly use meter 130 with test media from a brand or lot for which the meter 130 has not been calibrated.

Illustrative embodiments of the present invention provide one or more preventive measures that may disable one or more functions of the meter upon the occurrence of certain triggering events. For example, the preventive measure may render meter 130 wholly inoperative after the meter 130 has been used for a certain period of time or quantity of tests, or with a certain quantity of test media. The meter 130 may then be simply disposed of or returned to the manufacturer for remanufacturing. Alternatively, the preventive measure may render only the diagnostic testing function of controller 400 inoperative, or simply prevent the meter from displaying the result of a diagnostic test. The user may then retain meter 130 in order to use its remaining functions.

A given preventive measure may be triggered by the occurrence of a triggering event, such as the expiration of a certain time period. The time period may be related to particular test media, e.g., a particular container 110 or lot of test strips 120 for which meter 130 has been calibrated or otherwise associated. For example, a preventive measure may be triggered if the current date is after an expiration date of test media associated with the meter 130, e.g., where the manufacturer indicates that the particular test media should not be used more than two years after its date of manufacture. Alternatively, the expiration date may be determined relative to a date a particular container was opened, e.g., where the manufacturer indicates that the test media should not be used more than 2 months after its container 110 has first been opened.

The date a particular container 110 of test media has first been opened may be estimated or determined in a number of ways. For example, a detector 412 monitors the current draw of the LED 253 and relays the information to the meter 130, such that the meter 130 can ascertain when the vial 110 has been opened. This function need not be performed by a separate component, but may be performed by the controller 400. In addition, where meter 130 is precalibrated for use with a single container or lot of test strips, the date that the container has first been opened may be estimated by determining the date the meter was first turned on, e.g., by instructing controller 400 to save the date or start a timer when the meter 130 is first turned on or otherwise activated for use. However, because the user may turn on the meter (e.g., to familiarize themselves with the functions of the meter or to calibrate the meter) an indeterminate time before actually using the meter to conduct a diagnostic test, the date of first use of the meter can be estimated by instructing controller 400 to save the date or start a timer when meter 130 is first used to run a diagnostic test. Similarly, where meter 130 is calibrated by the user, the date a particular container is opened may be estimated by instructing controller 400 to save the date or start a timer when meter 130 is first used to conduct a diagnostic test after being calibrated or otherwise associated with a given plurality of test strips. Alternatively, where meter 130 is attached to a particular container 110, user control function 430 may include a switch actuated when the user opens the closure 140, e.g., so that the controller is informed when the container 110 is first opened. One having ordinary skill in the art will understand that other ways of determining first use of the container 110 are possible.

Moreover, an optical sensor, electrical measurement, mechanical switch or acoustic sensor can also be used to determine how long and the accumulated time the container 110 has been open. This information can be valuable in determining test strip 120 viability, or in the case of a humidity sensitive test strip 120, for example, if a test strip 120 can be recovered by placing it in a desiccated container 110 for a longer period of time.

In addition, when the container 110 of test media is opened, the meter 130 can automatically or selectively turn on the display 133. In other embodiments, controller 400 may be started or awakened from a sleep state when the container 110 is first opened.

Detector 412 may also monitor the current draw of the LED 253 and relay the information to the meter 130, such that the meter 130 can ascertain when the LED 253 has been illuminated. This function need not be performed by a separate component, but may be performed by the controller 400. Controller 400 is configured to start a timer upon determining that the light source 253 has been illuminated. Analogous to the method described above, the timer is designed to track an elapsed time from the first time a container 110 is opened by a user. In addition, the timer is also configured to signal the controller 400 to extinguish the light source 253 and alert the user after a predetermined time. The alert may be, for example, a visual, an audio, a kinetic, or a combination alarm.

The time period need not be related to a particular lot or container of test media. A particular preventive measure may be triggered a predetermined time after manufacture or first use of meter 130, or first use of a particular meter function (e.g., performance of a diagnostic test), without regard to any characteristic of the test media. For example, a given preventive measure may be triggered three months after first use of the meter to conduct a diagnostic test. In any case, indicator function 450 may be used to indicate the time remaining until preventive measures are triggered.

Alternatively or in addition, controller 400 may maintain a running count of the quantity of test media used or the quantity of diagnostic tests performed by the meter using the current calibration data. The quantity of test media used may be estimated by the number of times that test media have been inserted in media interface 410 or, preferably, the number of times a sample has been detected, e.g., by the media sensors. The running count may be compared to a quantity of tests or test media allowed before triggering of a preventive measure. The allowed quantity may relate to a quantity of test media that were originally packaged with meter 130 by the manufacturer or distributor, e.g., the quantity of test media originally contained in an associated container 110. As a further alternative, the allowed quantity may exceed the number of test strips contained in the associated packaging or container 110 by a small amount, e.g., 10%. If the running count exceeds the operative quantity, then a preventive measure may be triggered. Indicator function 450 may be used to indicate the quantity of diagnostic tests or test media remaining before a preventive measure is activated.

Information related to the trigger for the preventive measure (e.g., the allowed time period, the expiration date of the associated test media, the quantity of diagnostic tests, the quantity of diagnostic test strips, etc.) may be obtained in a manner similar to the calibration data. In an illustrative embodiment, controller 400 is distributed with the trigger information, e.g., encoded in memory 406 or elsewhere in controller 400. Alternatively, the trigger information may be entered by the user. For example, the trigger information may be appended to the calibration data that is entered or downloaded by the user. Alternatively, the user may enter or download the trigger information (or a code from which controller 400 may derive the trigger information) separately from the calibration data.

Controller 400 may be instructed to periodically determine whether a particular preventive measure is triggered. For example, controller 400 may determine whether a preventive measure is triggered on a daily or weekly basis. Alternatively or in addition, controller 400 may be instructed to determine whether a given preventive measure is triggered whenever a certain event occurs. For example, controller 400 may be instructed to determine whether a preventive measure is triggered whenever a test strip 120 is inserted into test strip interface 110, whenever a sample is detected by the media sensors, whenever a diagnostic test is performed by the controller, whenever the result of a diagnostic test is displayed, or whenever a certain user control 430 or other function of meter 130 is actuated, etc.

The preventive measures may take a number of forms. Where the power source 420 of the meter is finite (e.g., a battery), the preventive measure may manipulate the life of power source 420 so that the power source, e.g., a battery within housing 131, becomes inoperative soon after the preventive measure is triggered. For instance, controller 400 may increase the load on the power source when the preventive measure is triggered. The load may be increased, e.g., by raising the frequency of system clock 408 so that the rate power is consumed by the controller 400 and other electronic functions is increased. The power source 420, and thus meter 130, will then become inoperative in a relatively short period of time. Alternatively or in addition, controller 400 may be instructed to cause the meter 130 to remain in an "on" state once the preventive measure is triggered, thus draining the power source. As a further alternative, controller may be instructed to open a switch or blow a fuse so as to disconnect power source 420 from the electronic functions of the meter 130. For this embodiment, meter housing 131 may be constructed so that power source 420 is not replaceable. Indicator function 450 may indicate an estimation of the time remaining before the power source 420, and thus the meter 130, become inoperable.

Another preventive measure may prevent a diagnostic test from being performed. For example, where meter 130 includes an auto-on function for initiating a diagnostic test upon insertion of a test strip 120 into interface 410 (e.g., as set forth in U.S. Pat. Nos. 6,743,635 and 6,946,299, incorporated by reference above), controller 400 may be instructed to disable the auto-on function when the preventive measure is triggered. Controller 400 may nevertheless allow the user to turn on the meter using user control function 430 so as to allow access to other functions of the meter. For instance, controller 400 may allow the user to turn on the meter and review previous test results and/or associated voice messages stored in memory 406.

As another alternative, the preventive measure may allow the a diagnostic test to be performed, but prevent the indicator function from indicating the result. Instead, the meter may display a message indicating that the meter is not calibrated and/or that the meter needs to be replaced. As before, controller 400 may still allow the user to review previous test results and any associated voice messages stored in memory 406. The meter 130 itself may then be given or sent to the user's medical care provider. The medical care provider may then review the results of the diagnostic tests and/or associated voice messages for use in treating the user.

As a further preventive measure, controller 400 may be instructed to reconfigure the function of meter 130. For instance, controller 400 may instructed to reconfigure indicator function 450 to indicate other information in place of a result of a diagnostic test. For example, the indicator function 450 may be reconfigured to indicate the time and/or the date. Alternatively, indicator function 450 may be reconfigured to indicate readings from environmental sensors 480. For example, the meter 130 may indicate the temperature and/or humidity, together with the appropriate units, on display 133. As another alternative, controller 400 may be instructed to reconfigure the voice message function 470 to allow voice messages to be recorded for purposes other than indicating results of a diagnostic test.

The user control function 430 may be reconfigured in accordance with the reconfiguration of the indicator function. For example, the indicator function 450 may be reconfigured to act as a timer, e.g., a kitchen timer. User control 430 may be correspondingly reconfigured to control the timer. For example, user control 430 may be reconfigured to start and stop the timer. Alternatively, user control 430 may be reconfigured to switch between or adjust displays of the time, date, temperature and/or humidity.

The meter may be provided with a fastener (e.g., a magnet, a VELCRO hook and loop fastener, an adhesive, etc.) on its back so as to allow the user to place the meter 130 where its new function will be useful. For example, the user may place the meter on their refrigerator. In this manner, the user may be reminded of the meter manufacturer's or distributor's name and/or logo (which may be placed next to the display 133) in a context outside of the use of the meter 130 for diagnostic testing.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for diagnostic testing, comprising:
a container including a continuously connected interior volume permitting contact between with a plurality of loose, singulated test media housed therein,
a diagnostic meter body configured to close an opening of the container, and for performing a diagnostic test on a sample applied to the test media, the meter body comprising:
a first exterior surface configured to be an interior surface of the container when the container is closed by the meter body;
a second exterior surface configured to remain an exterior surface when the container is closed by the meter body;
an insertion port disposed on the second exterior surface, and configured to receive test media inserted from an exterior of the container and the meter;
an interface comprising at least one media sensor configured to engage the test media inserted into the insertion port from an exterior of the container and the meter; in order to perform the diagnostic test;
a controller configured to perform the diagnostic test;
an indicator for indicating a result of the diagnostic test;
a strip ejector mechanism to dispose of the test media; and
a data connector capable of establishing data communication with a computer.

2. The system for diagnostic testing of claim 1, wherein the data connector is a USB connector.

3. The system for diagnostic testing of claim 1, wherein the meter comprises a data storage device.

4. The system for diagnostic testing of claim 1, wherein the meter is configured to attach to a side portion of a container configured to contain test media compatible with the meter.

5. The system for diagnostic testing of claim 1, wherein the meter is integrated with a sampling device, forming a composite diagnostic testing device.

6. The system for diagnostic testing of claim 5, wherein the sampling device is a lancet.

7. The system for diagnostic testing of claim 5, wherein the meter and the sampling device are separate devices usable together.

8. The system for diagnostic testing of claim 7, wherein the meter and the sampling device are separate devices contained together by means of a clip.

9. The system for diagnostic testing of claim 7, wherein the meter and the sampling device are separate devices contained together by means of an attachment with a plurality of holes.

10. A system for diagnostic testing, the system comprising:
a meter for performing a diagnostic test on a sample applied to test media, the meter comprising:
a housing with an indicator for indicating a result of the diagnostic test;
a first exterior surface;
a second exterior surface;
an insertion port disposed on the second exterior surface, and configured to receive test media inserted from an exterior of the container and the meter;
an interface comprising at least one media sensor configured to engage the test media when it is inserted into the insertion port from an exterior of the container and the meter; in order to perform the diagnostic test; and
a container compatible with the meter, the container comprising:
an opening and a continuously connected interior volume permitting contact between a plurality of loose, singulated test media housed therein,
wherein the first exterior surface of the meter housing is configured to close the opening of the container,
wherein the second exterior surface of the meter housing is configured to remain exterior to the container when the opening of the container is closed by the first exterior surface;
wherein the container comprises a holder configured to receive one or more devices used for diagnostic testing, and
wherein the opening is accessible to a user of the system.

11. The system for diagnostic testing of claim 10, wherein the holder engages the meter.

12. The system for diagnostic testing of claim 10, wherein the holder engages a lancet.

* * * * *